US009682239B2

(12) United States Patent
Koop

(10) Patent No.: US 9,682,239 B2
(45) Date of Patent: Jun. 20, 2017

(54) SYSTEMS AND METHODS FOR TREATING CARDIAC ARRHYTHMIAS

(71) Applicant: CARDIAC PACEMAKERS, INC., St. Paul, MN (US)

(72) Inventor: Brendan E. Koop, Ham Lake, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 15/006,928

(22) Filed: Jan. 26, 2016

(65) Prior Publication Data

US 2016/0228712 A1 Aug. 11, 2016

Related U.S. Application Data

(60) Provisional application No. 62/113,147, filed on Feb. 6, 2015.

(51) Int. Cl.
*A61N 1/00* (2006.01)
*A61N 1/365* (2006.01)
*A61N 1/375* (2006.01)
*A61N 1/362* (2006.01)
*A61N 1/372* (2006.01)
(Continued)

(52) U.S. Cl.
CPC ....... *A61N 1/36514* (2013.01); *A61N 1/0573* (2013.01); *A61N 1/362* (2013.01); *A61N 1/368* (2013.01); *A61N 1/3756* (2013.01); *A61N 1/37205* (2013.01); *A61N 1/37288* (2013.01); *A61N 2001/0585* (2013.01)

(58) Field of Classification Search
CPC .. A61N 1/36514; A61N 1/0573; A61N 1/362; A61N 1/368; A61N 1/37205; A61N 1/37288; A61N 1/3756; A61N 2001/0585; A61N 1/057
See application file for complete search history.

(56) References Cited

U.S. PATENT DOCUMENTS 7,310,556 B2 12/2007 Bulkes
7,894,915 B1 2/2011 Chitre et al.
(Continued)

OTHER PUBLICATIONS

Notification of Transmittal of the International Search Report and the Written Opinion of the International Searching Authority, or the Declaration for Application No. PCT/US2016/014954, 16 pages, date mailed Jul. 19, 2016.
(Continued)

*Primary Examiner* — Robert N Wieland
(74) *Attorney, Agent, or Firm* — Seager, Tufte & Wickhem LLP.

(57) ABSTRACT

An implantable medical device (IMD) may include a housing having a proximal end and a distal end and a set of one or more electrodes connected to but spaced apart from the housing. The IMD may further include a controller disposed within the housing, wherein the controller is configured to sense cardiac electrical signals, and deliver electrical stimulation pulses via the first set of one or more electrodes. In some embodiments, a first portion of the housing is configured to be disposed at least partly within a coronary sinus of a patient's heart and a second portion of the housing is configured to be disposed at least partly within a right atrium of the patient's heart.

20 Claims, 25 Drawing Sheets

(51) Int. Cl.
*A61N 1/368* (2006.01)
*A61N 1/05* (2006.01)

(56) References Cited

U.S. PATENT DOCUMENTS

| | | | |
|---|---|---|---|
| 8,103,359 B2 | 1/2012 | Reddy | |
| 8,527,068 B2 | 9/2013 | Ostroff | |
| 8,571,678 B2 | 10/2013 | Wang | |
| 8,634,912 B2 | 1/2014 | Bornzin et al. | |
| 8,634,919 B1 * | 1/2014 | Hou | A61N 1/3756 607/122 |
| 8,644,934 B2 | 2/2014 | Hastings et al. | |
| 8,670,842 B1 | 3/2014 | Bornzin et al. | |
| 8,700,181 B2 | 4/2014 | Bornzin et al. | |
| 8,758,365 B2 | 6/2014 | Bonner et al. | |
| 8,781,605 B2 | 7/2014 | Bornzin et al. | |
| 2013/0023975 A1 | 1/2013 | Locsin | |
| 2013/0035748 A1 | 2/2013 | Bonner et al. | |
| 2013/0110127 A1 | 5/2013 | Bornzin et al. | |
| 2013/0110219 A1 | 5/2013 | Bornzin et al. | |
| 2013/0116529 A1 | 5/2013 | Min et al. | |
| 2013/0116738 A1 | 5/2013 | Samade et al. | |
| 2013/0116740 A1 | 5/2013 | Bornzin et al. | |
| 2013/0116741 A1 | 5/2013 | Bornzin et al. | |
| 2013/0123872 A1 | 5/2013 | Bornzin et al. | |
| 2013/0138006 A1 | 5/2013 | Bornzin et al. | |
| 2013/0325081 A1 | 12/2013 | Karst et al. | |
| 2013/0345770 A1 | 12/2013 | Dianaty et al. | |
| 2014/0100627 A1 | 4/2014 | Min | |
| 2014/0107723 A1 | 4/2014 | Hou et al. | |
| 2014/0172034 A1 | 6/2014 | Bornzin et al. | |
| 2014/0172060 A1 | 6/2014 | Bornzin et al. | |
| 2014/0243848 A1 | 8/2014 | Auricchio et al. | |
| 2014/0288576 A1 | 9/2014 | Bornzin et al. | |

OTHER PUBLICATIONS

Invitation to pay Additional fees and, Where Applicable, Protest fee for Application No. PCT/US2016/014954, 2016, 7 pages, date mailed Apr. 18, 2016.

* cited by examiner

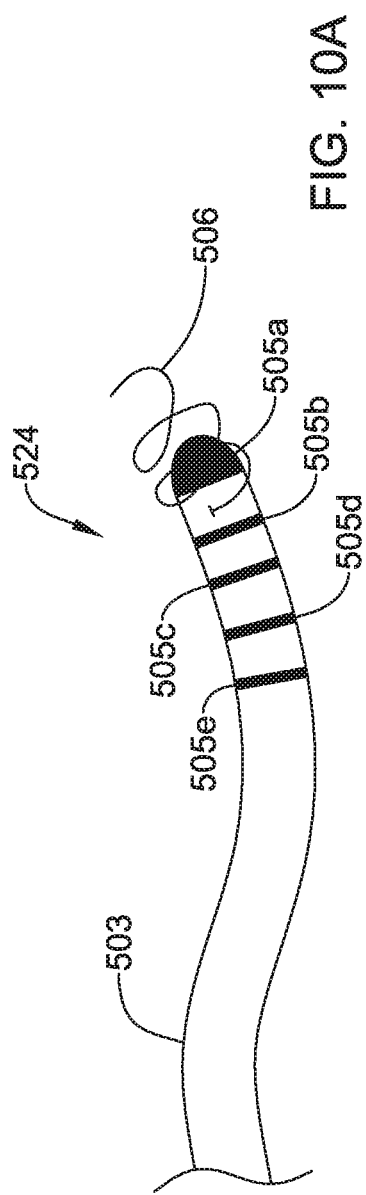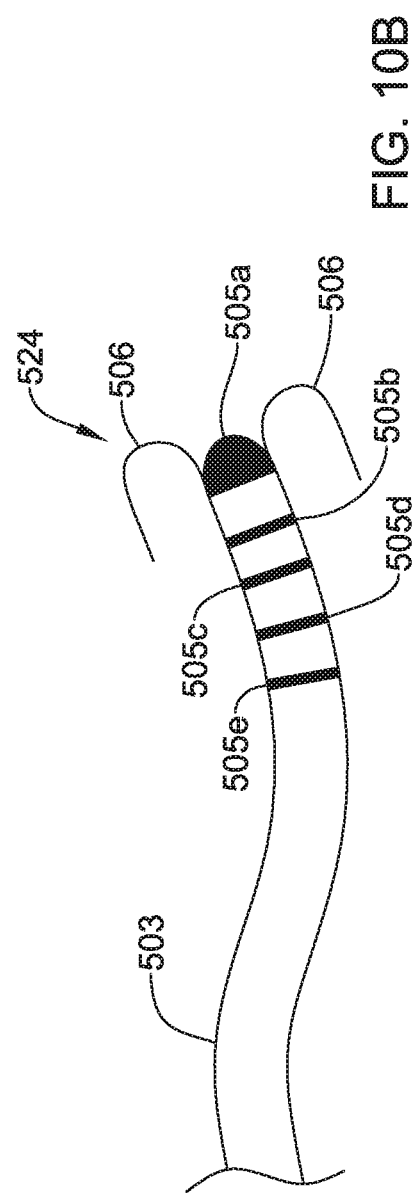

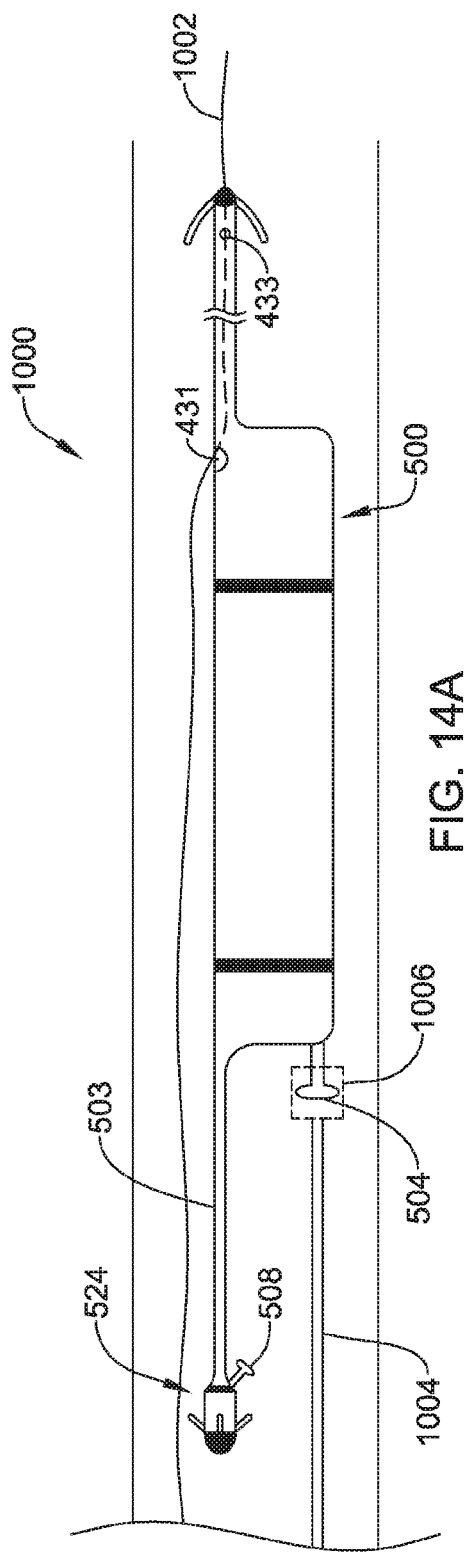
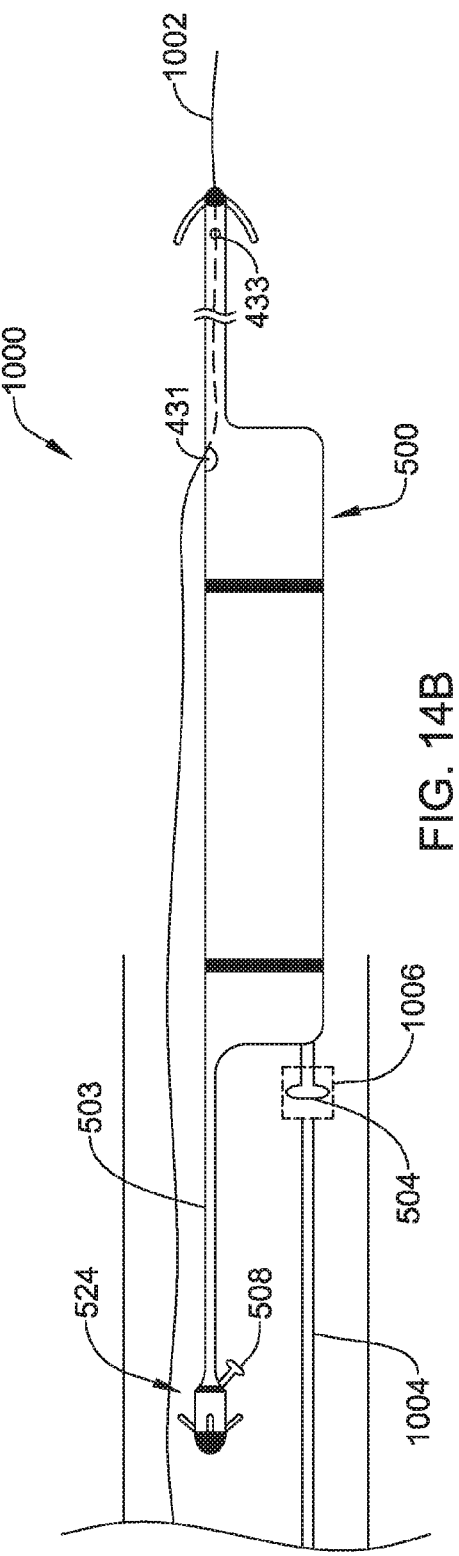

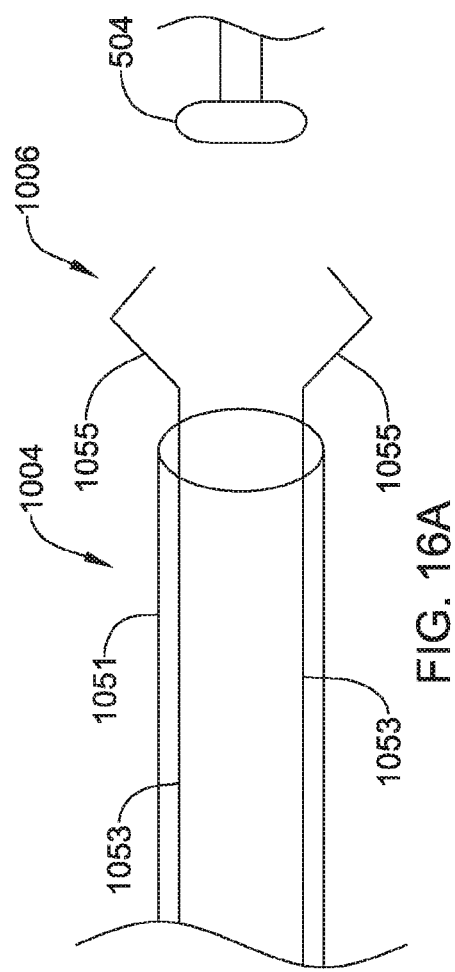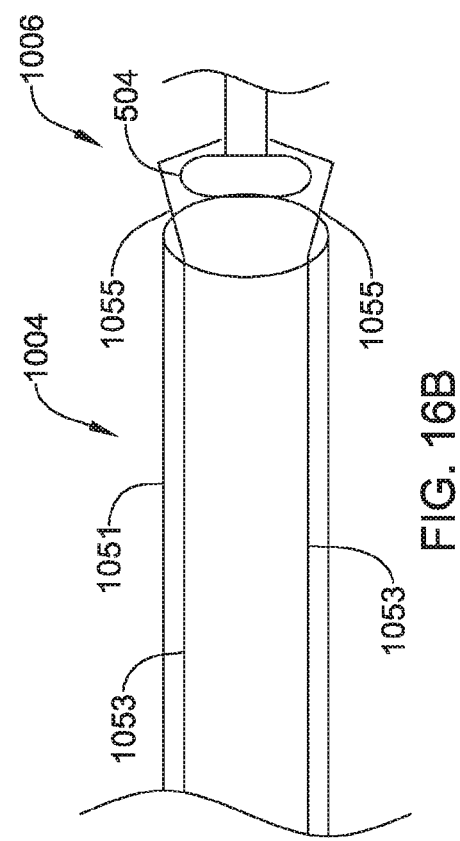

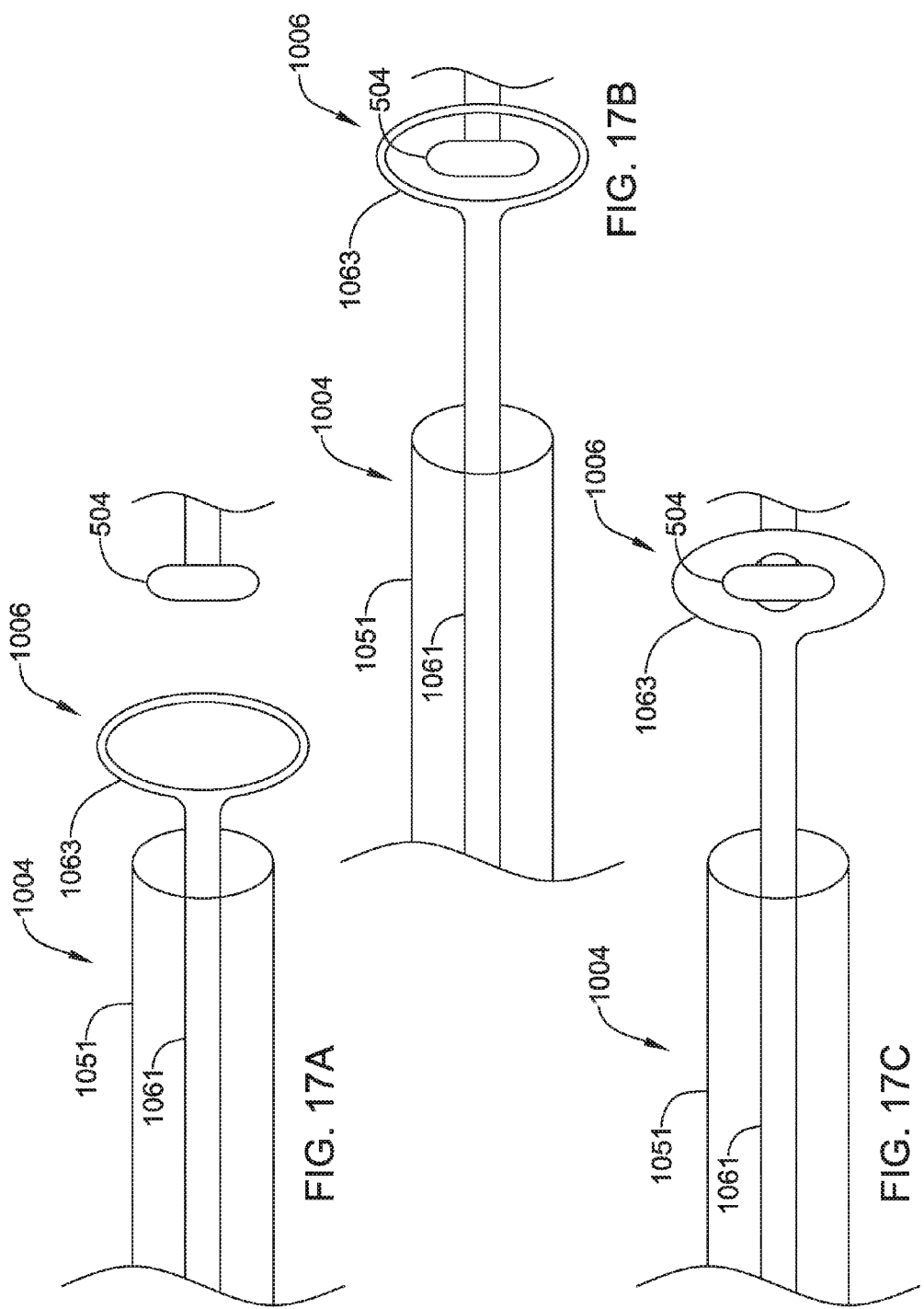

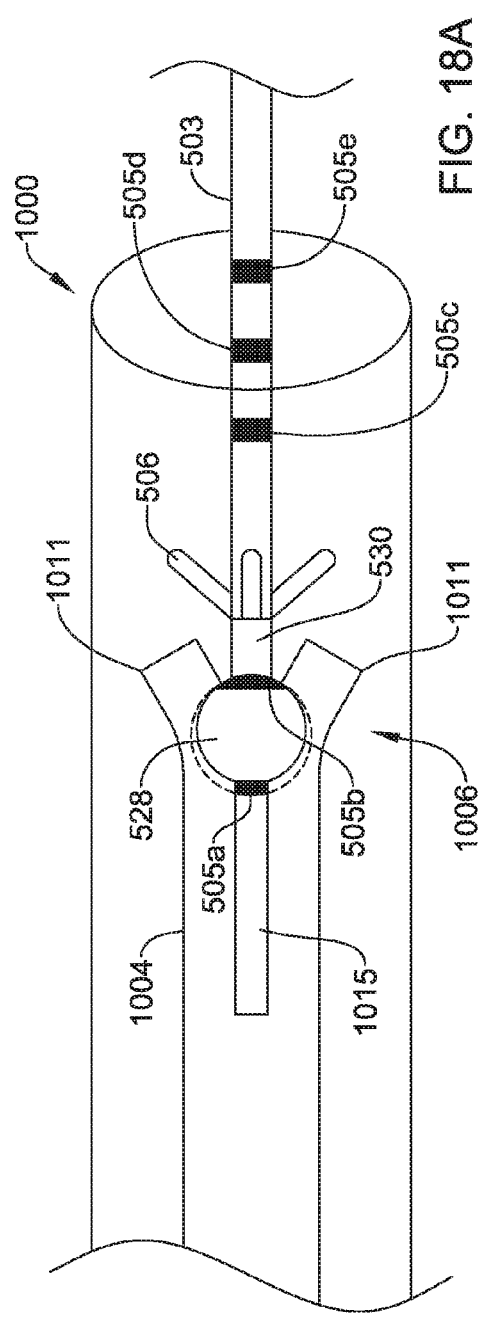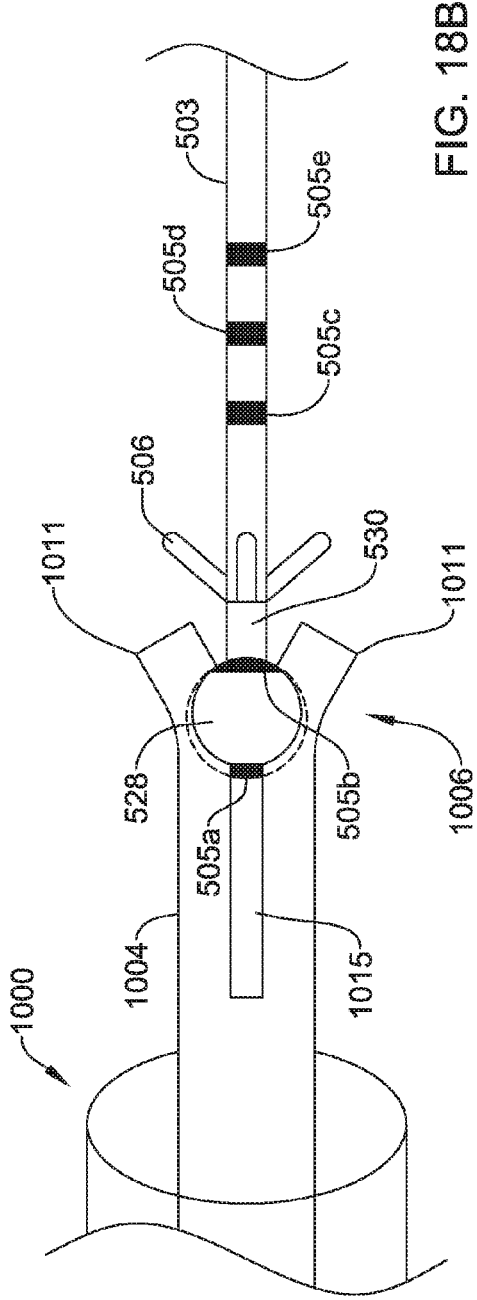

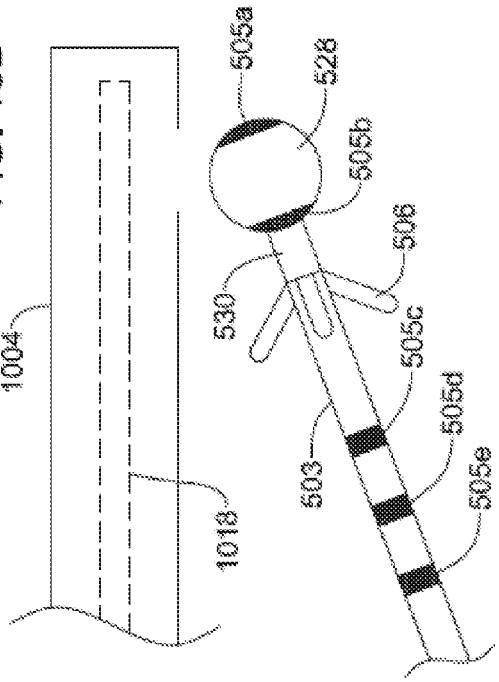
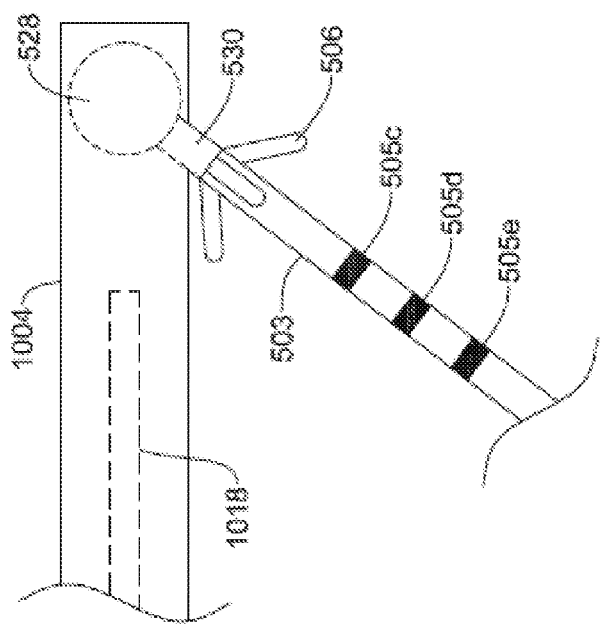

SYSTEMS AND METHODS FOR TREATING CARDIAC ARRHYTHMIAS

CROSS REFERENCE TO RELATED APPLICATIONS

This application claims the benefit of U.S. Provisional Patent Application Ser. No. 62/113,147 filed on Feb. 6, 2015, the disclosures of each incorporated herein by reference.

TECHNICAL FIELD

The present disclosure generally relates to systems, devices, and methods for treating cardiac arrhythmias, and more particularly, to systems, devices, and methods for detecting cardiac arrhythmias and delivering electrical stimulation therapy to a right atrium, left atrium and/or left ventricle of a heart.

BACKGROUND

Pacing instruments can be used to treat patients suffering from various heart conditions that result in a reduced ability of the heart to deliver sufficient amounts of blood to a patient's body. These heart conditions may lead to rapid, irregular, and/or inefficient heart contractions. To help alleviate some of these conditions, various devices (e.g., pacemakers, defibrillators, etc.) have been implanted in a patient's body. Such devices may monitor and provide electrical stimulation to the heart to help the heart operate in a more normal, efficient and/or safe manner.

SUMMARY

The present disclosure generally relates to systems, devices, and methods for treating cardiac arrhythmias, and more particularly, to systems, devices, and methods for detecting cardiac arrhythmias and delivering electrical stimulation therapy to a right atrium and/or a left ventricle of a heart.

In one embodiment, an implantable medical device (IMD) comprises a housing having a proximal end and a distal end and a first set of one or more electrodes connected to but spaced apart from the housing. In some embodiments, the IMD may also comprise a controller disposed within the housing. The controller may be configured to sense cardiac electrical signals, and deliver electrical stimulation pulses via the first set of one or more electrodes. In some embodiments, a first portion of the housing may be configured to be disposed at least partly within a coronary sinus of a patient's heart and a second portion of the housing is configured to be disposed at least partly within a right atrium of the patient's heart.

Alternatively, or additionally, in the embodiment above, the housing further comprises a fixation element disposed on the portion of the housing that is configured to be disposed within the coronary sinus.

Alternatively, or additionally, in any of the above embodiments, the housing further comprises an eccentric bias element disposed on the portion of the housing that is configured to be disposed within the coronary sinus.

Alternatively, or additionally, in any of the above embodiments, the housing further comprises a docking hub disposed proximate the proximal end of the housing.

Alternatively, or additionally, in any of the above embodiments, the docking hub is configured to extend into the right atrium of the patient's heart.

Alternatively, or additionally, in any of the above embodiments, the housing comprises at least a first discrete section and a second discrete section, and wherein the first discrete section is configured to be disposed at least partially within the coronary sinus and the second discrete section is configured to be disposed within the right atrium of the patient's heart.

Alternatively, or additionally, in any of the above embodiments, the first discrete section and the second discrete section are connected by a flexible connector section.

Alternatively, or additionally, in any of the above embodiments, the first discrete section comprises an energy storage device.

Alternatively, or additionally, in any of the above embodiments, the second discrete section comprises a processing module.

Alternatively, or additionally, in any of the above embodiments, at least a portion of the housing has a non-circular cross-section.

Alternatively, or additionally, in any of the above embodiments, the housing further comprises a guide-wire entrance port disposed on the first portion of the housing.

Alternatively, or additionally, in any of the above embodiments, the first set of one or more electrodes is configured to be disposed within the right atrium of the patient's heart.

Alternatively, or additionally, in any of the above embodiments, the first set of one or more electrodes are disposed on a first extension extending from the housing.

Alternatively, or additionally, in any of the above embodiments, the first extension has a proximal end and a distal end, and wherein the proximal end of the first extension is connected to the housing, and wherein a fixation element is positioned adjacent the distal end.

Alternatively, or additionally, in any of the above embodiments, the fixation element comprises one or more of tines, helical coils, and talons.

Alternatively, or additionally, in any of the above embodiments, a docking hub is positioned adjacent the distal end of the first extension.

Alternatively, or additionally, in any of the above embodiments, comprising a second set of one or more electrodes spaced apart from the housing.

Alternatively, or additionally, in any of the above embodiments, the second set of one or more electrodes are configured to be disposed within the coronary sinus.

Alternatively, or additionally, in any of the above embodiments, the second set of one or more electrodes are disposed on a second extension.

Alternatively, or additionally, in any of the above embodiments, the second extension has a proximal end and a distal end, and wherein the proximal end of the second extension is connected to the housing.

Alternatively, or additionally, in any of the above embodiments, the second extension further comprises one or more fixation elements, and wherein the one or more fixation elements comprise one or more of tines, helical coils, and metal talons.

Alternatively, or additionally, in any of the above embodiments, at least part of the second extension is coiled.

Alternatively, or additionally, in any of the above embodiments, the second extension further comprises a guide-wire exit port.

In another embodiment, an implantable medical device (IMD) comprises a housing having a proximal end and a distal end and a first set of one or more electrodes connected to but spaced apart from the housing. The IMD may further comprise a controller disposed within the housing, and the controller is configured to communicate with one or more medical devices spaced from the IMD, sense cardiac electrical signals, and deliver electrical stimulation pulses via the first set of one or more electrodes. In some embodiments, the housing is configured to be disposed at least partly within a coronary sinus of a patient's heart.

Alternatively, or additionally, in the above embodiment, the housing further includes a first portion and a second portion, and wherein the first a portion of the housing is configured to be disposed at least partly within the coronary sinus of the patient's heart and a second portion of the housing is configured to be disposed at least partly within a right atrium of the patient's heart.

Alternatively, or additionally, in any of the above embodiments, the first set of electrodes is configured to be disposed within the right atrium of the patient's heart, and the controller is configured to deliver electrical stimulation to the right atrium of the patient's heart via the first set of electrodes.

Alternatively, or additionally, in any of the above embodiments, the IMD further comprises a second set of one or more electrodes, and wherein the second set of one or more electrodes are configured to be disposed within the coronary sinus.

Alternatively, or additionally, in any of the above embodiments, the controller is configured to deliver electrical stimulation to a left ventricle of the patient's heart via the second set of one or more electrodes.

Alternatively, or additionally, in any of the above embodiments, the one or more medical devices comprise one or more of: an implantable cardioverter-defibrillator (ICD); a subcutaneous implantable cardioverter-defibrillator (SICD); an implantable cardiac pacemaker (ICD); an implantable leadless cardiac pacemaker (LCP); and a device programmer.

Alternatively, or additionally, in any of the above embodiments, the housing further comprises a docking hub disposed proximate the proximal end of the housing.

Alternatively, or additionally, in any of the above embodiments, the docking hub is configured to extend into the right atrium of the patient's heart.

Alternatively, or additionally, in any of the above embodiments, the housing comprises at least a first discrete section and a second discrete section, and wherein the first discrete section is configured to be disposed at least partially within the coronary sinus and the second discrete section is configured to be disposed within the right atrium of the patient's heart.

Alternatively, or additionally, in any of the above embodiments, the first discrete section and the second discrete section are connected by a flexible connector section.

Alternatively, or additionally, in any of the above embodiments, the first discrete section comprises an energy storage device.

Alternatively, or additionally, in any of the above embodiments, the second discrete section comprises a processing module.

In yet another embodiment, an implantable medical device (IMD) comprises a housing having a rigid first portion and a rigid second portion, wherein the rigid first portion and the rigid second portion are physically connected by a flexible connector. The IMD may additionally comprise a controller disposed within the housing, and the controller is configured to communicate with one or more medical devices spaced from the IMD, sense cardiac electrical signals, and deliver electrical stimulation pulses via a first set of one or more electrodes. In some embodiments, the rigid first portion of the housing is configured to be disposed at least partly within the right atrium of the patient's heart, and the rigid second portion of the housing is configured to be disposed at least partly within a coronary sinus of the patient's heart. Additionally, at least some embodiments may further comprise a fixation element for holding the rigid second portion of the housing at least partly within the coronary sinus of the patient's heart.

Alternatively, or additionally, in the above embodiment, the housing comprises a docking hub disposed on the rigid first portion.

Alternatively, or additionally, in any of the above embodiments, the first set of one or more electrodes are provided on an atrial extension extending from the rigid first portion, wherein the atrial extension includes a fixation element configured to fix the atrial extension to the an atrium wall of the atrium of the patient's heart.

Alternatively, or additionally, in any of the above embodiments, the fixation element comprises one or more of tines, a helical coil, or metal talons.

Alternatively, or additionally, in any of the above embodiments, further comprising a second set of one or more electrodes, wherein the second set of one or more electrodes are provided on a ventricle extension extending from the rigid second portion further into the coronary sinus of the patient's heart, wherein the ventricle extension includes a fixation element configured to fix the ventricle extension to a wall of the coronary sinus of the patient's heart.

Alternatively, or additionally, in any of the above embodiments, the controller is further configured to deliver electrical stimulation pulses via the second set of one or more electrodes.

In another embodiment, an implantable medical device (IMD), comprises an elongated housing and a first head spaced from the elongated housing but connected to the elongated housing via a first flexible connector, the first head comprising a first fixation element for fixing the first head to the heart of the patient. In some embodiments, the first head and/or the first flexible connector comprising one or more first electrodes. The IMD may further comprise a controller disposed within the elongated housing, wherein the controller is configured to deliver electrical stimulation pulses to the heart of the patient via one or more of the first electrodes of the first head.

Alternatively, or additionally, in the above embodiment, the elongated housing has a length and a maximum width, with a non-circular cross-section across the maximum width to facilitate blood flow past the elongated housing when the elongated housing is disposed at least partly within a coronary sinus of a heart of a patient.

Alternatively, or additionally, in any of the above embodiments, the elongated housing comprises a first docking hub.

Alternatively, or additionally, in any of the above embodiments, the first head comprises a second docking hub.

Alternatively, or additionally, in any of the above embodiments, the first fixation element is configured to pierce through at least part of the heart of the patient.

Alternatively, or additionally, in any of the above embodiments, further comprising a second head spaced from the elongated housing but connected to the elongated housing via a second flexible connector, the second head comprising a second fixation element for fixing the second head to the heart of the patient.

Alternatively, or additionally, in any of the above embodiments, the second fixation element comprises one or more of tines, helical coils, and talons.

Alternatively, or additionally, in any of the above embodiments, the second head and/or the second flexible connector comprising one or more second electrodes.

Alternatively, or additionally, in any of the above embodiments, the controller is further configured to deliver electrical stimulation pulses to the heart of the patient via one or more of the second electrodes of the second head.

Alternatively, or additionally, in any of the above embodiments, the housing comprises one or more housing electrodes.

Alternatively, or additionally, in any of the above embodiments, the controller is further configured to communicate with one or more medical devices spaced from the IMD.

Alternatively, or additionally, in any of the above embodiments, the controller is configured to communicate with one or more medical devices spaced from the IMD using one or more housing electrodes that are fixed relative to the elongated housing.

The above summary is not intended to describe each embodiment or every implementation of the present disclosure. Advantages and attainments, together with a more complete understanding of the disclosure, will become apparent and appreciated by referring to the following description and claims taken in conjunction with the accompanying drawings.

BRIEF DESCRIPTION OF THE DRAWINGS

The disclosure may be more completely understood in consideration of the following description of various illustrative embodiments in connection with the accompanying drawings, in which:

FIGS. 10A-10B are plan views of illustrative fixation elements for an extension of a pacing device;

FIGS. 14A-14B are illustrative diagrams showing an illustrative pacing device being pushed along a guide wire and out the distal end of a guide catheter;

FIGS. 16A-16B are diagrams of an illustrative interlocking mechanism for engaging and/or disengaging a docking hub of a pacing device;

FIGS. 17A-17C are illustrative diagrams of another illustrative interlocking mechanism for engaging and/or disengaging a docking hub of a pacing device;

FIGS. 18A-18D are illustrative diagrams of an illustrative interlocking mechanism for engaging and/or disengaging a portion of a pacing device.

Figure 1:
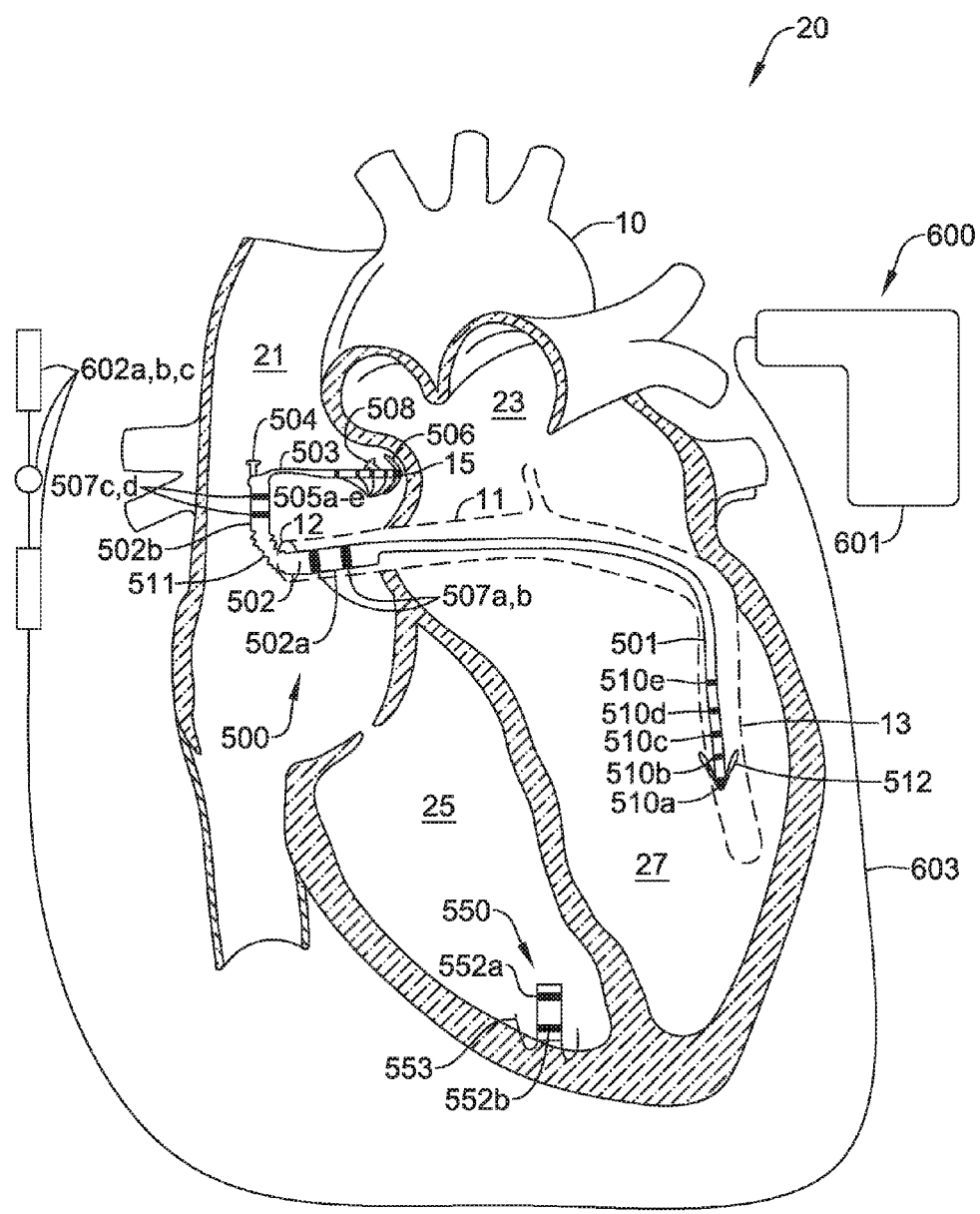
FIG. 1 is a schematic diagram of an illustrative medical device system.

While the disclosure is amenable to various modifications and alternative forms, specifics thereof have been shown by way of embodiment in the drawings and will be described in detail. It should be understood, however, that the intention is not to limit aspects of the disclosure to the particular illustrative embodiments described. On the contrary, the intention is to cover all modifications, equivalents, and alternatives falling within the spirit and scope of the disclosure.

DESCRIPTION

The following description should be read with reference to the drawings in which similar elements in different drawings are numbered the same. The description and the drawings, which are not necessarily to scale, depict illustrative embodiments and are not intended to limit the scope of the disclosure.

This disclosure describes systems, devices, and methods for detecting and treating cardiac arrhythmias, and more particularly, to systems, devices, and methods for delivering electrical stimulation therapy to a right atrium, left atrium and/or a left ventricle of a heart of a patient. For instance, one or more devices may be implanted on or within a patient's heart, and the one or more devices may be configured to deliver electrical stimulation therapy to one or more chambers of the patient's heart in accordance with one or more therapy programs and/or to treat one or more types of detected cardiac arrhythmias. Some example electrical stimulation therapies include bradycardia therapy, cardiac resynchronization therapy (CRT), anti-tachycardia pacing (ATP) therapy, defibrillation and/or cardioversion therapy, and the like. Some example cardiac arrhythmias include atrial fibrillation or atrial flutter, ventricular fibrillation, and tachycardia.

FIG. 1 is a conceptual diagram of an illustrative system for delivering electrical stimulation therapy to a patient's heart, including delivering electrical stimulation therapy to a right atrium, left atrium, and/or a left ventricle of the patient's heart. FIG. 1 shows an illustrative system 20 implanted in and around heart 10. Heart 10 of FIG. 1 is depicted showing right atrium 21, left atrium 23, right ventricle 25, left ventricle 27, coronary sinus 11, coronary sinus ostium 12, great cardiac vein 13, and septum 15.

FIG. 1 depicts system 20 as including a pacing device 500, a leadless cardiac pacemaker (LCP) 550, and an implantable cardioverter-defibrillator (ICD) 600. In the embodiment of FIG. 1, illustrative pacing device 500 includes housing or body 502 having a proximal end and a distal end and extensions 501, 503. However, in some instances, extension 501 and/or extension 503 may not be included. In some embodiments, body 502 may include two body portions 502a, 502b connected by connection 511, with body portion 502a disposed at the distal end of body 502 and body portion 502b disposed the proximal end of body 502. In some cases, connection 511 may be a flexible connection which may allow body portions 502a and 502b to move relative to one another. Additionally, when implanted, body portion 502a may be fully or partially disposed within coronary sinus 11 of the patient's heart, while body portion 502b may be disposed fully or partially within right atrium 21.

In some embodiments, pacing device 500 may additionally include one or more electrodes 507a-507d. Although electrodes 507a-507d are depicted as disposed on both body portions 502a, 502b, in some cases, the number and location of electrodes disposed on body 502 may vary, depending on the application. For example, pacing device 500 may only have electrodes disposed on one body portion 502a or 502b where pacing device 500 includes two body portions. In some instances, pacing device 500 may not have any electrodes disposed on body 502. When provided, electrodes 507a-507d may be used to deliver electrical stimulation to heart 10, and/or sense one or more physiologic signals. In some cases, pacing device 500 may use one or more of the electrodes 507a-507d to communicate with one or more other devices, such as LCP 550 and/or ICD 600. In some instances, pacing device 500 may communicate using conducted communication techniques, as will be described with respect to other figures, and may deliver and/or receive communication signals through one or more of the electrodes 507a-507d.

In some instances, body 502 may include a docking hub 504 which extends generally from the proximal end of body 502. In the example shown in FIG. 1, docking hub 504 may extend from body portion 502a. During implantation, docking hub 504 may be releasably coupled to a positioning device (not shown). When coupled, movement of the positioning device may translate to body 502, thereby allowing a user, such as a physician, to maneuver body 502 into a proper position within heart 10, for example into or proximate coronary sinus 11.

In some instances, docking hub 504 may be a retrieval hub. Accordingly, during implantation, docking hub may not releasably couple to a positioning device. Rather, pacing device 500 may be delivered from a guide catheter, and the portion of the guide catheter surrounding body 502 may conform to body 502 to create a secure connection between the guide catheter and body 502. When in position, the guide catheter may be retracted, or a stylet or other pushing device may push body 502 out of the guide catheter. In these cases, docking hub 504 may further include a tether anchor. During delivery, a tether may be coupled to the tether anchor to allow a user to pull body 502 back within the guide catheter for further positioning. In some instances, the tether is a string, and the string may be coupled to the tether anchor by looping around the tether anchor. To release the tether from body 502, a user may simply cut the tether or pull one end of the tether until the tether unloops itself from the tether anchor.

In some cases, body 502 may include extension 503 extending from the proximal end of body 502, or body portion 502b as shown in FIG. 1. When implanted, extension 503 may extend from body 502 to near septum 15 of heart 10. The distal end of extension 503 may include one or more fixation elements 506. Fixation elements 506 may secure the distal end of extension 503 in right atrium 21 proximate septum 15, or, in some instances, directly to septum 15. In some embodiments, fixation elements 506 may include one or more tines made of silicon, a biocompatible polymer, a biocompatible metal, or another biocompatible material. In such embodiments, the tines may be embedded within trabeculae of right atrium 21 proximate septum 15 to help provide a stable connection. In other embodiments, fixation elements 506 may comprise one or more of a helical coil or talons.

In some cases, extension 503 may include one or more electrodes 505a-505e. When provided, electrodes 505a-505e may be disposed proximate the distal end of extension 503, however in other embodiments, electrodes 505a-505e may span the length of extension 503. In this manner, in some embodiments, electrodes 505a-505e may be spaced apart from body 502. In some instances, some or all of electrodes 505a-505e may be used to deliver electrical stimulation to heart 10, and more particularly, to the right atrium of the heart. For instance, in the example shown in FIG. 1, pacing device 500 may deliver electrical stimulation to right atrium 21 of heart 10 through a set of one or more of the electrodes 505a-505e. As used herein, the set of electrodes by which pacing device 500 may deliver electrical stimulation may be termed the second set, and the set of electrodes by which pacing device 500 may deliver communication signals may be termed the first set. The second set of electrodes may include any pair of electrodes 505a-505e. Although, in other embodiments, the second set of electrodes may include more than two electrodes, and in general may include any combination of electrodes 505a-505e. In general, examples of electrical stimulation may include pacing pulses delivered in accordance with one or more programmed electrical stimulation therapies. In some cases, pacing device 500 may use one or more of the electrodes 505a-505e to communicate with one or more other devices. For instance, pacing device 500 may communicate using conducted communication techniques, as will be described with respect to other figures, and may deliver and/or receive communication signals through one or more of the electrodes 505a-505e.

In some cases, extension 503 may include a docking hub 508, which may extend from the proximal end of extension 503. During implantation, docking hub 508 may be releasably coupled to a positioning device (not shown). When coupled, movement of the positioning device may translate to the proximal end of extension 503, thereby allowing a user, such as physician, to maneuver the proximal end extension 503 into position within heart 10, for example proximate septum 15.

Although extension 501 is depicted in FIG. 1, in some embodiments, pacing device 500 may not include extension 501 and/or extension 503. Where pacing device 500 includes both extensions 501 and 503, extension 501 may extend from the distal end of body 502, for example body portion 502a, as shown in FIG. 1. When included, extension 501 may extend into coronary sinus 12 and be secured within coronary sinus 12. In some cases, extension 501 may extend through coronary sinus 12 and into great cardiac vein 13, as depicted in FIG. 1. The distal end of extension 501 may include one or more fixation elements 512. Fixation elements 512 may help secure the distal end of extension 501 within coronary sinus 12 or great cardiac vein 13. Fixation elements 512 may include one or more tines made of silicon, a biocompatible polymer, a biocompatible metal, or another biocompatible material. In such embodiments, the tines may extend outward from extension 501 and press against the walls of great cardiac vein 13. The friction between the tines and the walls of great cardiac vein 13 may hold the distal end of extension 501 in place. In other embodiments, fixation elements 512 may comprise one or more of a helical coil and talons.

Extension 501 may include one or more electrodes 510a-510e. In some of these embodiments, electrodes 510a-510e may be disposed proximate the distal end of extension 501 and away from body 502, however in other embodiments, electrodes 510a-510e may span the length of extension 501.

Accordingly, in this manner, electrodes 510a-510e may be spaced apart from body 502. In some cases, electrodes 510a-510e may be used to deliver electrical stimulation to heart 10. For example, pacing device 500 may deliver electrical stimulation to the left ventricle 27 of heart 10 through a set of one or more of electrodes 510a-510e. Where pacing device 500 does deliver electrical stimulation to left ventricle 27, the second set of electrodes mentioned above may additionally include any of electrodes 510a-510e. Although, pacing device 500 may use different electrode combinations from the second set of electrodes to deliver electrical stimulation to right atrium 21, left atrium 23, and/or left ventricle 27. Additionally, or alternatively, in some cases, pacing device 500 may deliver electrical stimulation to the left ventricle 27 of heart 10 using two or more of electrodes 510a-510e, either simultaneously or with a delay (e.g. via multi-electrode pacing). In still some additional or alternative cases, pacing device 500 may use one or more of the electrodes 510a-510e to communicate with one or more other devices. For instance, pacing device 500 may communicate using conducted communication techniques, as will be described with respect to other figures, and may deliver and/or receive communication signals through one or more of the electrodes 510a-510e.

In some cases, system 20 may include only pacing device 500 implanted as a single device (e.g. without LCP 550 or ICD 600), which may provide electrical stimulation to the right atrium 21, left atrium 23, and/or left ventricle 27, as desired. For instance, pacing device 500 may be configured to deliver electrical stimulation in accordance with a therapy program to treat atrial fibrillation or atrial flutter. However, in other cases, such as depicted in FIG. 1, system 20 may additionally include an LCP 550, such as the an LCP 550 in the right ventricle. Although LCP 550 is depicted implanted in right ventricle 25, in some cases, an LCP 550 may be implanted in other chambers of heart 10, such as left atrium 23, or left ventricle 27, or at various locations on the outside of heart 10. In some cases, system 20 may include multiple LCP devices implanted at various locations.

Where system 20 includes LCP 550 implanted within right ventricle 25 in addition to pacing device 500, LCP 550 and pacing device 500 may be configured to deliver electrical stimulation therapy to heart 10. For instance, LCP 550 may be configured to deliver electrical stimulation therapy to right ventricle 25 by delivering pacing pulses to the right ventricle 25 in a pattern according to a therapy program, sometimes including rate-responsive pacing, and/or delivering anti-tachycardia pacing (ATP) therapy. In embodiments including both pacing device 500 and LCP 550, system 20 may be configured to deliver electrical stimulation therapies such as ATP, CRT, and/or other electrical stimulation therapies to treat cardiac abnormalities such as bradycardia, tachycardia, ventricular desynchronization, atrial fibrillation or atrial flutter, and ventricular fibrillation.

In some embodiments, pacing device 500 may be part of a single or multiple device system for delivering cardiac resynchronization therapy (CRT) to heart 10. In some of these embodiments, pacing device 500 may sense cardiac electrical signals in one or more of right atrium 21 and left atrium 23. Once pacing device 500 senses cardiac electrical signals propagating through right atrium 21 and/or left atrium 23, pacing device 500 may deliver a pacing pulse to left ventricle 27 after a delay period (e.g. an AV delay). The length of the delay period may be determined or chosen such that pacing device 500 may deliver a pacing pulse to left ventricle 27 as the propagating cardiac electrical signals reach right ventricle 25 and cause right ventricle 25 to contract. In this manner, pacing device 500 may operate to provide synchronous contractions of right ventricle 25 and left ventricle 27. In some additional embodiments, pacing device 500 may adjust the delay period based on a sensed heart rate. For instance, when pacing device 500 senses an increased heart rate, pacing device 500 may shorten the length of the delay period. Conversely, when pacing device 500 senses a lowered heart rate, pacing device 500 may lengthen the delay period.

In other embodiments, pacing device 500 may deliver pacing pulses to right atrium 21 and/or left atrium 23. In these embodiments, pacing device may begin counting the delay period at the time of or just after pacing device 500 delivers a pacing pulse to right atrium 21 and/or left atrium 23. As with the previously described embodiments, this may cause synchronous contractions of right ventricle 25 and left ventricle 27. Where pacing device 500 is part of a system with an LCP implanted within right ventricle 25, pacing device 500 may communicate a trigger to the LCP after pacing device 500 delivers a pacing pulse to right atrium 21 and/or left atrium 23. After receiving the trigger, the LCP may deliver a pacing pulse to right ventricle 25 after its own delay period. In at least some of the examples, the delay period of the LCP and the delay period of pacing device 500 may be in alignment such that both the LCP and pacing device 500 deliver pacing pulses to right ventricle 25 and left ventricle 27 synchronously. However, in other embodiments, the delay period of the LCP and the delay period of pacing device 500 may be different, for instance if conduction through right ventricle 25 and left ventricle 27 differ, in order to cause right ventricle 25 and left ventricle 27 to contract synchronously.

As depicted in FIG. 1, LCP 550 may include one or more fixation members 553. In the example shown, the one or more fixation members 553 may secure LCP 550 within right ventricle 25. Additionally, LCP 550 may include electrodes 552a, 552b. In some cases, LCP 550 may include another electrode (not shown) near the fixation members 553 to engage the heart tissue. Where LCP 550 is configured to deliver electrical stimulation therapy, LCP 550 may deliver electrical stimulation therapy via electrodes 552a, 552b and/or another electrode. Additionally, LCP 550 may be configured to communicate with one or more other devices. In such embodiments, and where LCP 550 is configured to communicate using conducted communication, LCP 550 may be configured to deliver and/or receive communication signals via one or more of the electrodes 552a, 552b.

In some instances, system 20 may include an implantable cardioverter-defibrillator (ICD) 600. ICD 600 may include housing 601, lead 603, and electrodes 602a-602c, which in some embodiments may be spaced apart from housing 601. For example, electrodes 602a-602c may be located on one or more leads attached to housing 601. In some embodiments, ICD 600 is a subcutaneous ICD (SICD), and lead 603 may be a subcutaneously implanted lead as shown in FIG. 1. In some cases, ICD 600 may be configured to deliver electrical stimulation to heart 10. For instance, ICD 600 may be configured to deliver cardioversion and/or defibrillation therapy to heart 10. In such embodiments, ICD 600 may deliver such electrical stimulation therapy via one or more electrodes 602-602c. In some cases, ICD 600 may be configured to communicate with one or more other devices. Where ICD 600 is configured to communicate via conducted communication, ICD 600 may be configured to send and/or receive communication signals via one or more of the electrodes 602a-602c.

Figure 2:
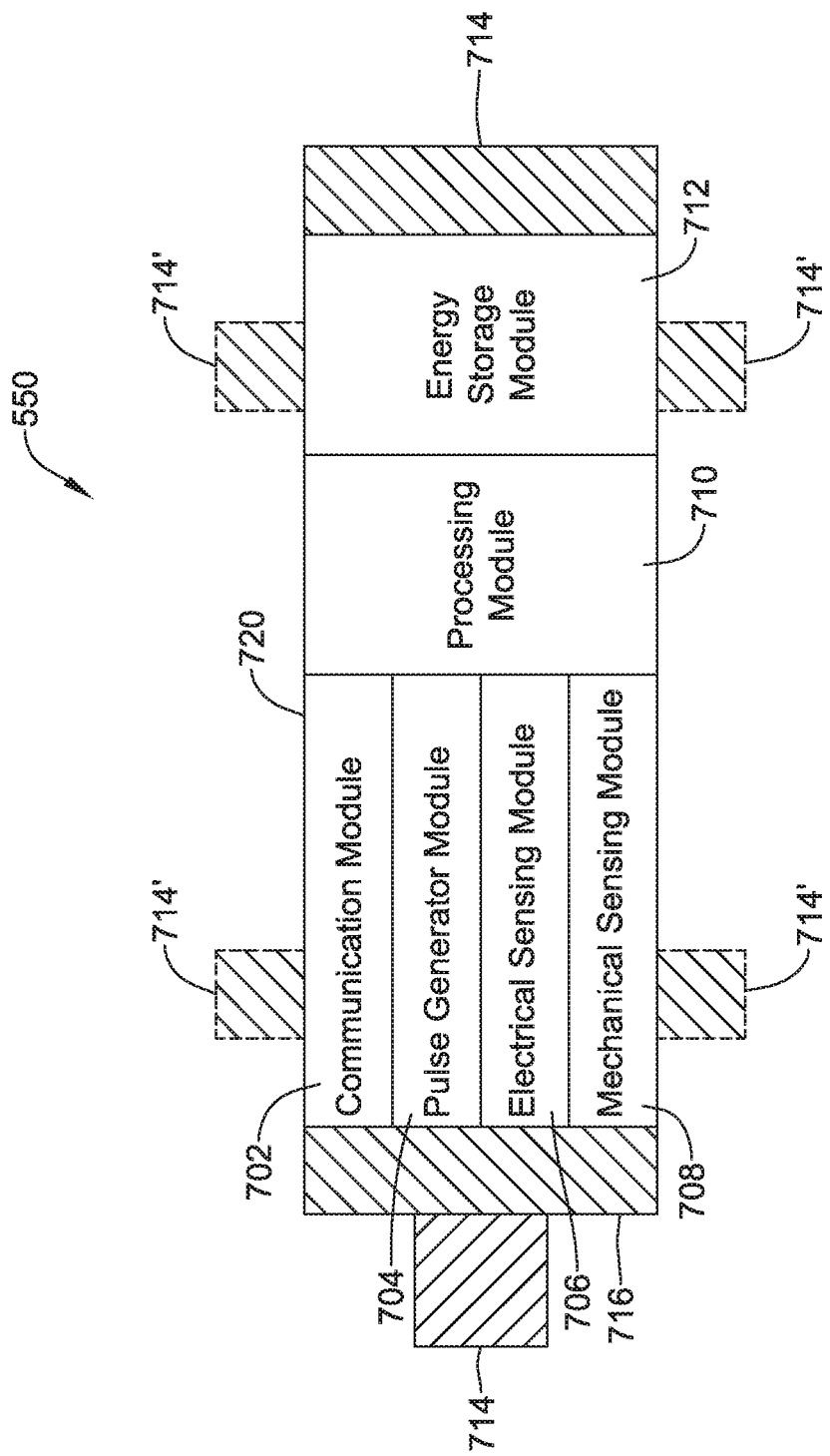
FIG. 2 is a schematic block diagram of an illustrative leadless cardiac pacemaker.

FIG. 2 is a conceptual schematic of an exemplary LCP 550 that may be used in system 20. Generally, LCP 550 may operate to sense physiological signals and parameters and deliver one or more types of electrical stimulation therapy to tissues of the patient. As can be seen in FIG. 2, LCP 550 may be a compact device with all components housed within LCP 550 or directly on housing 720. LCP 550 may include communication module 702, pulse generator module 704, electrical sensing module 706, mechanical sensing module 708, processing module 710, energy storage module 712, and electrodes 714.

As depicted in FIG. 2, LCP 550 may include electrodes 714, which can be secured relative to housing 720 and electrically exposed to tissue and/or blood surrounding LCP 550. Electrodes 714 may generally conduct electrical signals to and from LCP 550 and the surrounding tissue and/or blood. Such electrical signals can include electrical communication signals, electrical stimulation pulses, and intrinsic cardiac electrical signals, to name a few. Intrinsic cardiac electrical signals may include electrical signals generated by the heart and may be represented by an electrocardiogram (ECG).

Electrodes 714 may include one or more biocompatible conductive materials such as various metals or alloys that are known to be safe for implantation within a human body. In some instances, electrodes 714 may be generally disposed on either end of LCP 550 and may be in electrical communication with one or more of modules 702, 704, 706, 708, and 710. In embodiments where electrodes 714 are secured directly to housing 720, an insulative material may electrically isolate the electrodes 714 from adjacent electrodes, housing 720, and/or other parts of LCP 550. In some instances, some or all of electrodes 714 may be spaced from housing 720 and connected to housing 720 and/or other components of LCP 550 through connecting wires. In such instances, the electrodes 714 may be placed on a tail (not shown) that extends out away from the housing 720. As shown in FIG. 2, in some embodiments, LCP 550 may include electrodes 714'. Electrodes 714' may be in addition to electrodes 714, or may replace one or more of electrodes 714. Electrodes 714' may be similar to electrodes 714 except that electrodes 714' are disposed on the sides of LCP 550. In some cases, electrodes 714' may increase the number of electrodes by which LCP 550 may deliver electrical communication signals and/or electrical stimulation pulses, and/or may sense intrinsic cardiac electrical signals, electrical communication signals, and/or electrical stimulation pulses.

Electrodes 714 and/or 714' may assume any of a variety of sizes and/or shapes, and may be spaced at any of a variety of spacings. For example, electrodes 714 may have an outer diameter of two to twenty millimeters (mm). In other embodiments, electrodes 714 and/or 714' may have a diameter of two, three, five, seven millimeters (mm), or any other suitable diameter, dimension and/or shape. Example lengths for electrodes 714 and/or 714' may include, for example, one, three, five, ten millimeters (mm), or any other suitable length. As used herein, the length is a dimension of electrodes 714 and/or 714' that extends away from the outer surface of the housing 720. In some instances, at least some of electrodes 714 and/or 714' may be spaced from one another by a distance of twenty, thirty, forty, fifty millimeters (mm), or any other suitable spacing. The electrodes 714 and/or 714' of a single device may have different sizes with respect to each other, and the spacing and/or lengths of the electrodes on the device may or may not be uniform.

In the embodiment shown, communication module 702 may be electrically coupled to electrodes 714 and/or 714' and may be configured to deliver communication signals, such as electrical communication pulses, to tissues of the patient for communicating with other devices such as sensors, programmers, other medical devices, and/or the like. Electrical communication pulses, as used herein, may be any modulated signal that conveys information to another device, either by itself or in conjunction with one or more other modulated signals. In some embodiments, electrical communication pulses may be limited to sub-threshold signals that do not result in capture of the heart yet still convey information. The electrical communication pulses may be delivered to another device that is located either external or internal to the patient's body. Communication module 702 may additionally be configured to sense for electrical communication pulses delivered by other devices, which may be located external or internal to the patient's body.

Communication module 702 may communicate to help accomplish one or more desired functions. Some example functions include delivering sensed data, using communicated data for determining occurrences of events such as arrhythmias, coordinating delivery of electrical stimulation therapy, and/or other functions. In some cases, LCP 550 may use electrical communication pulses to communicate raw information, processed information, messages and/or commands, and/or other data. Raw information may include information such as sensed electrical signals (e.g. a sensed ECG), signals gathered from coupled sensors, and the like. In some embodiments, the processed information may include signals that have been filtered using one or more signal processing techniques. Processed information may also include parameters and/or events that are determined by the LCP 550 and/or another device, such as a determined heart rate, timing of determined heartbeats, timing of other determined events, determinations of threshold crossings, expirations of monitored time periods, activity level parameters, blood-oxygen parameters, blood pressure parameters, heart sound parameters, and the like. Messages and/or commands may include instructions or the like directing another device to take action, notifications of imminent actions of the sending device, requests for reading from the receiving device, requests for writing data to the receiving device, information messages, and/or other messages commands.

In at least some embodiments, communication module 702 (or LCP 550) may further include switching circuitry to selectively connect one or more of electrodes 714 and/or 714' to communication module 702 in order to select which electrodes 714 and/or 714' that communication module 702 delivers electrical communication pulses. It is contemplated that communication module 702 may communicate with other devices via conducted signals, radio frequency (RF) signals, optical signals, acoustic signals, inductive coupling, and/or any other suitable communication methodology.

In the embodiment shown, a pulse generator module 704 may be electrically connected to one or more of electrodes 714 and/or 714'. Pulse generator module 704 may be configured to generate electrical stimulation pulses and deliver the electrical stimulation pulses to tissues of a patient via one or more of the electrodes 714 and/or 714' in order to effectuate one or more electrical stimulation therapies. Electrical stimulation pulses as used herein are meant to encompass any electrical signals that may be delivered to tissue of a patient for purposes of treatment of any type of disease or abnormality. For example, when used to treat heart disease, the pulse generator module 704 may generate electrical stimulation pacing pulses for capturing the heart of the patient, i.e. causing the heart to contract in response to the delivered electrical stimulation pulse. In another embodiment, the electrical stimulation pulses may be defibrillation/cardioversion pulses for shocking the heart out of fibrillation. In yet another embodiment, the electrical stimulation pulses may be anti-tachycardia pacing (ATP) pulses. These are just some examples. When used to treat other ailments, the pulse generator module 704 may generate electrical stimulation pulses suitable for neurostimulation therapy or the like. Pulse generator module 704 may include one or more capacitor elements and/or other charge storage devices to aid in generating and delivering appropriate electrical stimulation pulses. In the embodiment shown, pulse generator module 704 may use energy stored in energy storage module 712 to generate the electrical stimulation pulses.

Pulse generator module 704 may include the capability to modify the electrical stimulation pulses, such as by adjusting the pulse width and/or amplitude of the electrical stimulation pulses. When pacing the heart, this may help tailor the electrical stimulation pulses to capture the heart a particular patient, sometimes with reduced battery usage. For neurostimulation therapy, adjusting the pulse width and/or amplitude may help tailor the therapy for a particular application and/or help make the therapy more effective for a particular patient.

Although depicted as separate modules, in some embodiments, LCP 550 may include a combined communication module 702/pulse generator module 704. For instance, pulse generator module 704 may be configured to also generate electrical communication pulses. In such embodiments, pulse generator 704 may be configured to generate and deliver both electrical communication pulses and electrical stimulation pulses.

In some embodiments, LCP 550 may include an electrical sensing module 706 and mechanical sensing module 708. Electrical sensing module 706 may be configured to sense intrinsic cardiac electrical signals conducted from electrodes 714 and/or 714' to electrical sensing module 706. For example, electrical sensing module 706 may be electrically connected to one or more electrodes 714 and/or 714' and electrical sensing module 706 may be configured to receive cardiac electrical signals conducted through electrodes 714 and/or 714'. In some embodiments, the cardiac electrical signals may represent local information from the chamber in which LCP 550 is implanted. For instance, if LCP 550 is implanted within a ventricle of the heart, cardiac electrical signals sensed by LCP 550 through electrodes 714 and/or 714' may represent ventricular cardiac electrical signals. Mechanical sensing module 708 may include, or be electrically connected to, various sensors, such as accelerometers, blood pressure sensors, heart sound sensors, blood-oxygen sensors, and/or other sensors which measure one or more physiological parameters of the heart and/or patient. Mechanical sensing module 708, when present, may gather signals from the sensors indicative of the various physiological parameters. Both electrical sensing module 706 and mechanical sensing module 708 may be connected to processing module 710 and may provide signals representative of the sensed cardiac electrical signals and/or physiological signals to processing module 710. Although described with respect to FIG. 2 as separate sensing modules, in some embodiments, electrical sensing module 706 and mechanical sensing module 108 may be combined into a single module.

Processing module 710 may be configured to control the operation of LCP 550. For example, processing module 710 may be configured to receive cardiac electrical signals from electrical sensing module 706 and/or physiological signals from mechanical sensing module 708. Based on the received signals, processing module 710 may determine, for example, occurrences and types of arrhythmias. Processing module 710 may further receive information from communication module 702. In some embodiments, processing module 710 may additionally use such received information to determine occurrences and types of arrhythmias. However, in other embodiments, LCP 550 may use the received information instead of the signals received from electrical sensing module 706 and/or mechanical sensing module 708—for instance if the received information is more accurate than the signals received from electrical sensing module 706 and/or mechanical sensing module 708 or if electrical sensing module 706 and/or mechanical sensing module 708 have been disabled or omitted from LCP 700.

Based on a determined arrhythmia, processing module 710 may control pulse generator module 704 to generate electrical stimulation pulses in accordance with one or more electrical stimulation therapies to treat the determined arrhythmia. For example, processing module 710 may control pulse generator module 704 to generate pacing pulses with varying parameters and in different sequences to effectuate one or more electrical stimulation therapies. For example, in controlling pulse generator module 704 to deliver bradycardia pacing therapy, processing module 710 may control pulse generator module 704 to deliver pacing pulses designed to capture the heart of the patient at a regular interval to help prevent the heart of a patient from falling below a predetermined threshold. In some cases, the rate of pacing may be increased with an increased activity level of the patient (e.g. rate adaptive pacing). For ATP therapy, processing module 710 may control pulse generator module 704 to deliver pacing pulses at a rate faster than an intrinsic heart rate of a patient in attempt to force the heart to beat in response to the delivered pacing pulses rather than in response to intrinsic cardiac electrical signals. Once the heart is following the pacing pulses, processing module 710 may control pulse generator module 704 to reduce the rate of delivered pacing pulses down to a safer level. In CRT, processing module 710 may control pulse generator module 704 to deliver pacing pulses in coordination with another device to cause the heart to contract more efficiently. In cases where pulse generator module 704 is capable of generating defibrillation and/or cardioversion pulses for defibrillation/cardioversion therapy, processing module 710 may control pulse generator module 704 to generate such defibrillation and/or cardioversion pulses. In some cases, processing module 710 may control pulse generator module 704 to generate electrical stimulation pulses to provide electrical stimulation therapies different than those examples described above.

Aside from controlling pulse generator module 704 to generate different types of electrical stimulation pulses and in different sequences, in some embodiments, processing module 710 may also control pulse generator module 704 to generate the various electrical stimulation pulses with varying pulse parameters. For example, each electrical stimulation pulse may have a pulse width and a pulse amplitude. Processing module 710 may control pulse generator module 704 to generate the various electrical stimulation pulses with specific pulse widths and pulse amplitudes. As one example, processing module 710 may cause pulse generator module 704 to adjust the pulse width and/or the pulse amplitude of electrical stimulation pulses if the electrical stimulation pulses are not effectively capturing the heart. Such control of the specific parameters of the various electrical stimulation pulses may help LCP 550 provide more effective delivery of electrical stimulation therapy.

In some embodiments, processing module 710 may further control communication module 702 to send information to other devices. For example, processing module 710 may control communication module 702 to generate one or more electrical communication pulses for communicating with other devices of a system of devices. For instance, processing module 710 may control communication module 702 to generate electrical communication pulses in particular sequences, where the specific sequences convey different information. Communication module 702 may also receive communication signals for potential action by processing module 710.

In further embodiments, processing module 710 may control switching circuitry by which communication module 702 and pulse generator module 704 deliver electrical communication pulses and/or electrical stimulation pulses to tissue of the patient. As described above, both communication module 702 and pulse generator module 704 may include circuitry for connecting one or more electrodes 714 and/714' to communication module 702 and/or pulse generator module 704 so those modules may deliver the electrical communication pulses and electrical stimulation pulses to tissue of the patient. The specific combination of one or more electrodes by which communication module 702 and/or pulse generator module 704 deliver electrical communication pulses and electrical stimulation pulses may influence the reception of communication pulses and/or the effectiveness of electrical stimulation pulses. Although it was described that each of communication module 702 and pulse generator module 704 may include switching circuitry, in some embodiments, LCP 550 may have a single switching module connected to the communication module 702, the pulse generator module 704, and electrodes 714 and/or 714'. In such embodiments, processing module 710 may control the switching module to connect modules 702/704 and electrodes 714/714' as appropriate.

In some embodiments, processing module 710 may include a pre-programmed chip, such as a very-large-scale integration (VLSI) chip or an application specific integrated circuit (ASIC). In such embodiments, the chip may be pre-programmed with control logic in order to control the operation of LCP 550. By using a pre-programmed chip, processing module 710 may use less power than other programmable circuits while able to maintain basic functionality, thereby potentially increasing the battery life of LCP 550. In other instances, processing module 710 may include a programmable microprocessor or the like. Such a programmable microprocessor may allow a user to adjust the control logic of LCP 550 after manufacture, thereby allowing for greater flexibility of LCP 550 than when using a pre-programmed chip.

Processing module 710, in additional embodiments, may include a memory circuit and processing module 710 may store information on and read information from the memory circuit. In other embodiments, LCP 550 may include a separate memory circuit (not shown) that is in communication with processing module 710, such that processing module 710 may read and write information to and from the separate memory circuit. The memory circuit, whether part of processing module 710 or separate from processing module 710, may be volatile memory, non-volatile memory, or a combination of volatile memory and non-volatile memory.

Energy storage module 712 may provide a power source to LCP 550 for its operations. In some embodiments, energy storage module 712 may be a non-rechargeable lithium-based battery. In other embodiments, the non-rechargeable battery may be made from other suitable materials. In some embodiments, energy storage module 712 may include a rechargeable battery. In still other embodiments, energy storage module 712 may include other types of energy storage devices such as super capacitors.

To implant LCP 550 inside a patient's body, an operator (e.g., a physician, clinician, etc.), may fix LCP 550 to the cardiac tissue of the patient's heart. To facilitate fixation, LCP 550 may include one or more anchors 716. Anchor 716 may include any number of fixation or anchoring mechanisms. For example, anchor 716 may include one or more pins, staples, threads, screws, helix, tines, and/or the like. In some embodiments, although not shown, anchor 716 may include threads on its external surface that may run along at least a partial length of anchor 716. The threads may provide friction between the cardiac tissue and the anchor to help fix anchor 716 within the cardiac tissue. In other embodiments, anchor 716 may include other structures such as barbs, spikes, or the like to facilitate engagement with the surrounding cardiac tissue.

Figure 3:
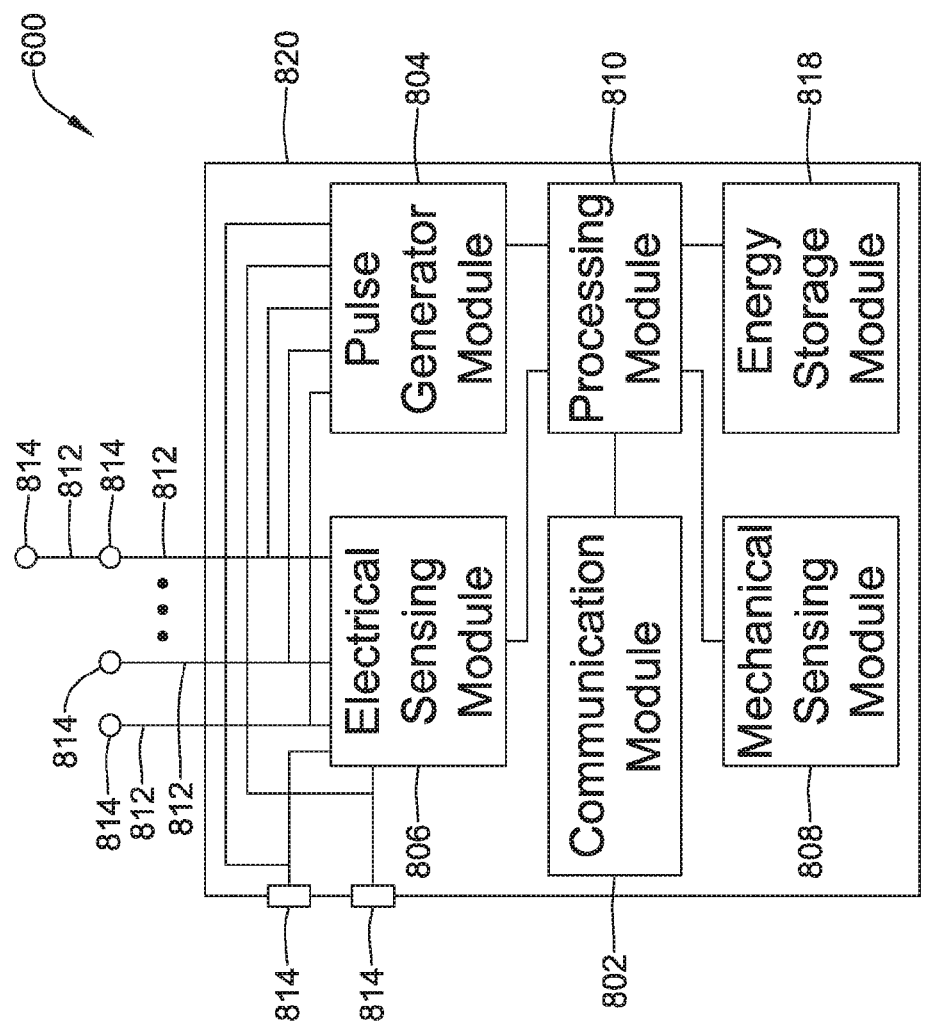
FIG. 3 is a schematic block diagram of an illustrative implantable cardioverter-defibrillator.

FIG. 3 depicts an embodiment of ICD 600, which may operate to sense physiological signals and/or parameters and deliver one or more types of electrical stimulation therapy to tissues of the patient. In the embodiment shown, ICD 600 may include a communication module 802, a pulse generator module 804, an electrical sensing module 806, a mechanical sensing module 808, a processing module 810, and an energy storage module 818. Each of modules 802, 804, 806, 808, and 810 may be similar to modules 702, 704, 706, 708, and 710 of LCP 550. Additionally, energy storage module 818 may be similar to energy storage module 712 of LCP 550. In some embodiments, however, ICD 600 may have a larger volume within housing 820. In such embodiments, ICD 600 may include a larger energy storage module 818 and/or a larger processing module 810 capable of handling more complex operations than processing module 710 of LCP 550.

As illustrated in FIG. 3, ICD 600 may include one or more leads 812. Leads 812 may include electrical wires that conduct electrical signals between electrodes 814 and one or more modules located within housing 820. In some cases, leads 812 may be connected to and extend away from housing 820 of ICD 600. In some embodiments, leads 812 may be implanted on, within, or adjacent to a heart of a patient. Leads 812 may contain one or more electrodes 814 positioned at various locations on leads 812 and various distances from housing 820. Some leads 812 may only include a single electrode 814, while other leads 812 may include multiple electrodes 814. Generally, electrodes 814 are positioned on leads 812 such that when leads 812 are implanted within the patient, one or more of the electrodes 814 are positioned to perform a desired function. In some cases, the one or more of the electrodes 814 may be in contact with the patient's cardiac tissue. In other cases, the one or more of the electrodes 814 may be positioned subcutaneously but adjacent the patient's heart, as are electrodes 602a-602c depicted in FIG. 1. The electrodes 814 may conduct intrinsically generated electrical cardiac signals to leads 812. Leads 812 may, in turn, conduct the received electrical cardiac signals to one or more of the modules 802, 804, 806, and 808 of ICD 600. In some cases, ICD 600 may generate electrical stimulation signals, and leads 812 may conduct the generated electrical stimulation signals to electrodes 814. Electrodes 814 may then conduct the electrical stimulation signals to the cardiac tissue of the patient (either directly or indirectly). ICD 600 may also include one or more electrodes 814 not disposed on a lead 812. For example, one or more electrodes 814 may be connected directly to housing 820.

Leads 812, in some embodiments, may additionally contain one or more sensors, such as accelerometers, blood pressure sensors, heart sound sensors, blood-oxygen sensors, and/or other sensors which are configured to measure one or more physiological parameters of the heart and/or patient. In such embodiments, mechanical sensing module 808 may be in electrical communication with leads 812 and may receive signals generated from such sensors.

Where housing 820 is implantable, housing 820 may be implanted in, for example, a transthoracic region of the patient. Housing 820 may generally include any of a number of known materials that are safe for implantation in a human body and may, when implanted, hermetically seal the various components of ICD 600 from fluids and tissues of the patient's body. In such embodiments, leads 812 may be implanted at one or more various locations within the patient, such as within the heart of the patient, adjacent to the heart of the patient, adjacent to the spine of the patient, or any other desired location.

In some embodiments, ICD 600 may be configured to sense electrical cardiac signals, determine occurrences of tachyarrhythmias based on the sensed electrical cardiac signals, and deliver defibrillation and/or cardioversion therapy in response to determining an occurrence of a tachyarrhythmia (for example by delivering defibrillation and/or cardioversion pulses to the heart of the patient). Where ICD 600 is a subcutaneous implantable cardioverter-defibrillator (SICD), although not required in all such embodiments, one of leads 812 may be a subcutaneously implanted lead. In at least some of these embodiments ICD 600 may include only a single lead which is implanted subcutaneously but outside of the chest cavity.

Figure 4:
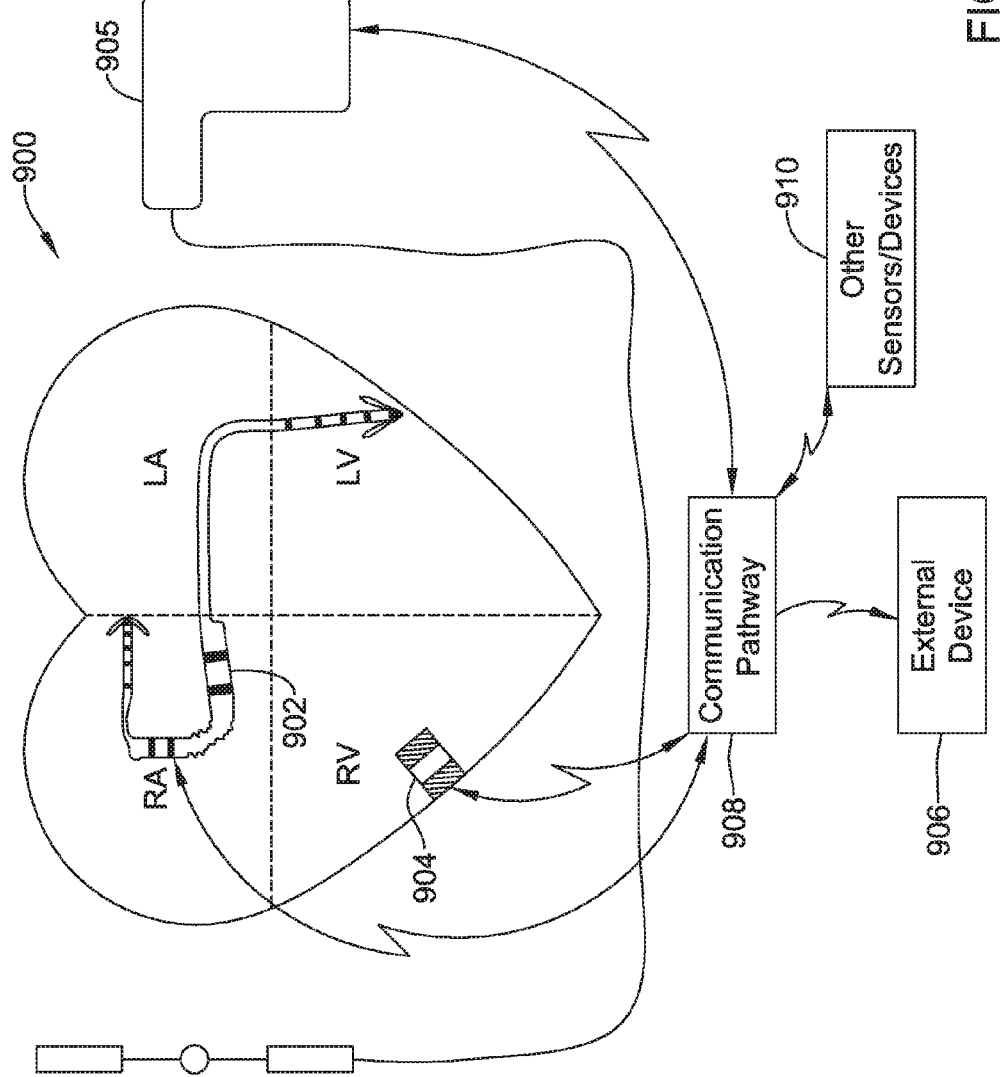
FIG. 4 is a schematic diagram of an illustrative system that includes an LCP and another medical device.

FIG. 4 illustrates an example medical device system 900 and a communication pathway through which multiple medical devices 902, 904, 905, 906, and/or 910 of system 900 may communicate. In the example shown, medical device system 900 may include pacing device 902, LCP 904, ICD 905, external medical device 906, and other sensors/devices 910. External device 906 may be a device disposed external to a patient's body. Other sensors/devices 910 may be, for example, various diagnostic sensors that gather information about the patient, such as accelerometers, blood pressure sensors, or the like. These sensors can be internal or external of the patient's body. In some cases, other sensors/devices 910 may include an external programmer device that may be used to program one or more devices of system 900.

In the example shown in FIG. 4, various devices of system 900 may communicate via communication pathway 908. For instance, pacing device 902, LCP 904, and/or ICD 905 may sense intrinsic cardiac electrical signals and may communicate such signals, or events based on such signals, to one or more other devices 902, 904, 905, 906, and 910 of system 900 via communication pathway 908. In one embodiment, one or more of devices 902, 904, and 905 may receive such signals and, based on the received signals, determine an occurrence of an arrhythmia or other physiological condition. In some cases, device or devices 902, 904, and/or 905 may communicate such determinations to one or more other devices 906 and 910 of system 900. In some cases, one or more of devices 902, 904, 905, 906, and 910 of system 900 may take action based on the communicated determination of an arrhythmia or other physiological condition, such as by delivering a suitable electrical stimulation to the heart of the patient. One or more of devices 902, 904, 905, 906, and 910 of system 900 may additionally communicate command or response messages via communication pathway 908. The command messages may cause a receiving device to take a particular action, whereas response messages may include requested information or a confirmation that a receiving device did, in fact, receive a communicated message or data.

It is contemplated that the various devices of system 900 may communicate via pathway 908 using conducted signals, RF signals, inductive coupling, optical signals, acoustic signals, or any other signals suitable for communication. In some instances, the various devices of system 900 may communicate via pathway 908 using different signal types. For instance, other sensors/device 910 may communicate with external device 906 using a first signal type (e.g. RF communication) but may communicate with pacing device 902 and/or LCP 904 using a second signal type (e.g. conducted communication). Further, in some embodiments, communication between devices may be limited. For instance, in some embodiments, pacing device 902 and/or LCP 904 may communicate with external device 906 only through other sensors/devices 910, where pacing device 902 and/or LCP 904 may send signals to other sensors/devices 910, and other sensors/devices 910 relay the received signals to external device 906. However, this is just one contemplated example.

In some cases, the various devices of system 900 may communicate via pathway 908 using conducted communication signals. Accordingly, devices of system 900 may have components that allow for such conducted communication. For instance, the devices of system 900 may be configured to transmit conducted communication signals (e.g. current and/or voltage pulses) into the patient's body via one or more electrodes of a transmitting device, and may receive the conducted communication signals (e.g. pulses) via one or more electrodes of a receiving device. The patient's body may "conduct" the conducted communication signals (e.g. pulses) from the one or more electrodes of the transmitting device to the electrodes of the receiving device in the system 900. In such embodiments, the delivered conducted communication signals (e.g. pulses) may differ from pacing pulses, defibrillation and/or cardioversion pulses, or other electrical stimulation therapy signals. For example, the devices of system 900 may deliver electrical communication pulses at an amplitude/pulse width that is sub-threshold (e.g. does not capture the heart, phrenic nerve, and/or other tissue). Although, in some cases, the amplitude/pulse width of the delivered electrical communication pulses may be above a capture threshold, but may be delivered during an irrelevant time period. For example, the amplitude/pulse width of the delivered electrical communication pulses may be above a capture threshold of the heart, but may be delivered during a refractory period of the heart and/or may be incorporated in or modulated onto a pacing pulse, as desired.

Delivered electrical communication pulses may be modulated in any suitable manner to encode communicated information. In some cases, the communication pulses may be pulse width modulated and/or amplitude modulated. Alternatively, or in addition, the time between pulses may be modulated to encode desired information. In some cases, conducted communication pulses may be voltage pulses, current pulses, biphasic voltage pulses, biphasic current pulses, or any other suitable electrical pulse as desired.

In the example of FIG. 1, system 20 may be communicatively coupled in any number of ways in different embodiments. For instance, in some embodiments, ICD 600 may be the only device which delivers electrical communication pulses, while pacing device 500 and/or LCP 550 may only be configured to receive electrical communication pulses. In other embodiments, all devices of system 20 may be configured to deliver electrical communication pulses and/or receive electrical communication pulses. In embodiments where pacing device 500 is configured to deliver electrical communication pulses, pacing device 500 may be configured to deliver electrical communication pulses via one or more different combinations of electrodes 507a-507d, 505a-505e, and/or 510a-510e. For instance, when delivering an electrical communication pulse, pacing device 500 may deliver electrical communication pulses via a first set of electrodes. The first set of electrodes may be any pair of electrodes from between electrodes 507a-507d, 505a-505e, and 510a-510e. As one example, pacing device 500 may deliver communication pulses via a first set of electrodes that includes electrodes 505a and 505e, or electrodes 505b and 507a, or some other combination. In some cases, the particular set of electrodes that is used may change over time. Although, in other embodiments, the first set of electrodes may comprise any combination of any number of electrodes from electrodes 507a-507d, 505a-505e, and 510a-510e.

In some instances, pacing device 500 may use a different set of electrodes by which to deliver electrical communication pulses depending for which device the electrical communication pulses are intended. For example, pacing device 500 may deliver electrical communication pulses via one particular set of electrodes if the electrical communication pulses are intended for LCP 550. However, if the electrical communication pulses are intended for ICD 600, pacing device may deliver the electrical communication pulses via another set of electrodes that is a different combination of electrodes than the electrodes pacing device 500 uses to deliver electrical communication pulses intended for LCP 550. Although, in some instances, pacing device 500 may use the same set of electrodes when delivering electrical communication pulses intended for any device.

Additionally, pacing device 500 may use still another, different set of electrodes when receiving communication signals. The receiving set of electrodes may be different from the communicating set of electrodes, but this is not required.

LCP 550 and ICD 600 may deliver electrical communication pulses and receive communication signals in a similar manner as pacing device 500. For example, LCP 550 and ICD 600 may use a desired combination of their electrodes to deliver electrical communication pulses and/or to receive communication signals. Additionally, LCP 550 and/or ICD 600 may, in some embodiments, use different vectors when communicating with different devices. However, in some cases, LCP 550 and/or ICD 600 may use the same vector when communicating with different devices.

Figure 5:
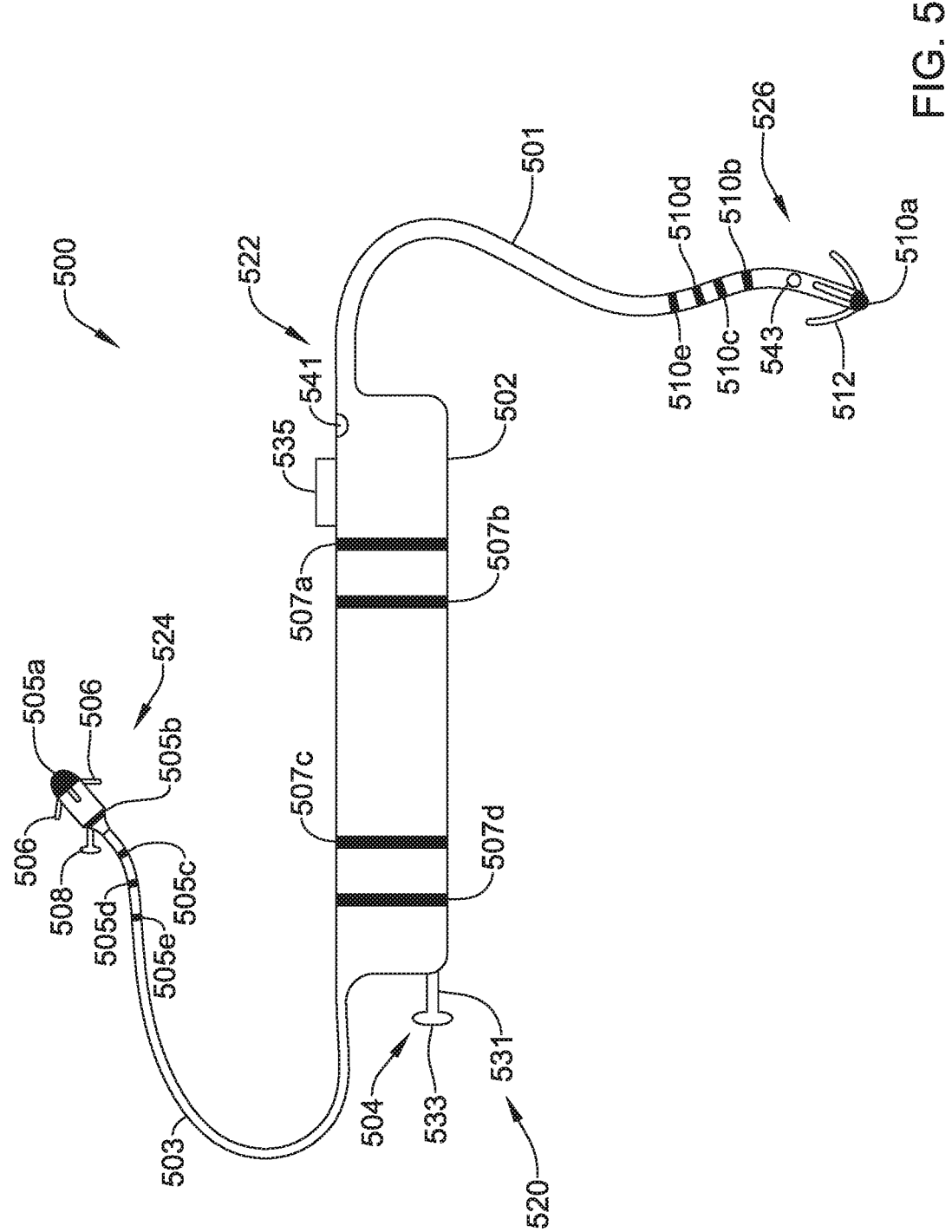
FIG. 5 is a schematic diagram of an illustrative pacing device.

FIG. 5 is a schematic diagram of an illustrative pacing device 500. The example pacing device 500 includes body 502 having a proximal end 520 and a distal end 522, sometimes with extensions 501 and/or 503. In some cases, extension 501 and/or extension 503 may not be included. In some cases, the extensions 501 and/or 503 may be integrally formed with the body 502. In other cases, the extensions 501 and/or 503 and body 502 are modular components, where one or more appropriate extensions 501 and/or 503 may be selected by a physician for a particular application and connected to the body 502. Body 502 may be a unitary housing in which one or more components of pacing device 500 are housed. Body 502 may generally include a biocompatible material, such as a biocompatible metal or polymer, and, when implanted within a patient's body, may hermetically seal the components of pacing device 500 from fluids and tissues of the patient's body. Pacing device 500 may additionally have one or more electrodes, such as electrodes 507a-507d, which in the example shown, reside on body 502. It is contemplated in some cases that body 502 may have a different number of electrodes, or no electrodes at all.

In some instances body 502 may include a docking hub 504 extending from proximal end 520. In some cases, docking hub 504 may have an extension 531 projecting from body 502 connected to an appendage 533. In the example shown in FIG. 5, appendage 533 may have a greater diameter than extension 531. During implantation, a positioning device may releasably couple to docking hub 504. When coupled, movement of the positioning device may translate to body 502, thereby allowing a user to position pacing device 500 during implantation. In some cases, instead of extension 531 and appendage 533, docking hub 504 may include one-half of an interlocking mechanism, and the positioning device may have the second half of the interlocking mechanism, which may releasably couple to the interlocking mechanism of docking hub 504.

In some instances, body 502 may include a fixation mechanism 535. Fixation mechanism 535 may be configured to maintain pacing device 100 within coronary sinus 11 when pacing device 500 is implanted within the coronary sinus of the heart 10. In at least some additional embodiments, fixation mechanism 535 may further maintain body 502 in a desired disposition with respect to the lumen of coronary sinus 11, for instance floating in the middle of the lumen or pressed up against the wall of coronary sinus 11. For instance, fixation mechanism 535 may include one or more tines or talons that may embed within the wall of coronary sinus 11 when pacing device 500 is implanted. In other instances, body 502 may not include fixation mechanism 535. In such embodiments, pacing device 502 may be held within coronary sinus 11 between extension 501 and 503, each of which may be secured in place. In embodiments where pacing device 100 does not include extension 501, pacing device 500 may include a fixation mechanism extending from distal end 522. For instance, pacing device 500 may include one or more fixation elements similar to fixation elements 506 or 512. In other embodiments, pacing device 500 may include a coiled extension, where the coiled extension has a greater diameter than the diameter of coronary sinus 11. The friction between the coiled extension and the walls of coronary sinus 11 may help hold pacing device 500 in place within the coronary sinus 11.

In at least some embodiments, body 502 may have guide wire port 541. In some cases, guide wire port 541 may be disposed proximate distal end 522 of body 502 and may be configured to receive a guide wire. Where pacing device 500 includes extension 501, extension 501 may include a corresponding guide wire port 543 located proximate distal end 526 of extension 501. In such embodiments, a guide wire may be placed down the great cardiac vein 13. The pacing device 500 may be tracked over the guide wire by threading extension 501 over the proximal end of the guide wire, and then advancing the pacing device 500 over the guide wire until in position. In embodiments where pacing device 500 does not include extension 501, body 502 may include a second guide wire port.

In some cases, body 502 may include extension 503 extending from proximal end 520 of the body 502. Generally, extension 503 may be a thin and flexible member, particularly in relation to body 502. For instance, extension 503 may be between two and ten times the length of body 502. Extension 503 may contain one or more electrical conductors that electrically connect electrodes 505a-505e residing on extension 503 with one or more components within body 502. In some embodiments, electrodes 505a-505e may be disposed proximate distal end 524 of extension 503. However, in other embodiments, electrodes 505a-505e may be disposed along the length of extension 503. In some instances, distal end 524 of extension 503 may terminate in an electrode, such as electrode 505a. Extension 503 may have a different number of electrodes, or no electrodes at all. Accordingly, in this manner, electrodes 505a-505e may be spaced apart from body 502. In some cases, one or more of the electrodes 505a-505e are spaced apart from a body 502 that is located in the coronary sinus 11 by a sufficient distance to electrically engage the septum 15 of the right atrium 21.

In some embodiments, extension 503 may be biased to form a shape that directs the distal end 524 toward the septum 15 of the right atrium 21. Distal end 524 of extension 503 may sometimes include one or more fixation elements 506. When pacing device 500 is implanted, fixation elements 506 may help secure the distal end 524 of extension 503 in right atrium 21 proximate septum 15, or, in some embodiments, to septum 15. In some instances, extension 503 may include a docking hub 508 which extends proximally from the distal end 524 of extension 503. In some instances, docking hub 508 may be similar to docking hub 504. For example, docking hub 508 may include an extension and an appendage. Or, docking hub 508 may include one-half of an interlocking mechanism. In at least some instances, docking hub 508 may releasably couple to the same positioning device that may releasably couple to docking hub 504. As with docking hub 504, when docking hub 508 is releasably coupled to the positioning device, movement of the positioning device may translate to the distal end 524 of extension 503 thereby allowing a user to maneuver the distal end 524 of extension 503 into position within heart 10.

As mentioned, in some instances, pacing device 500 may optionally include extension 501 extending from distal end 522 of body 502. Extension 501 may be similar to extension 503 in that extension 501 may be a thin and flexible member, particular in relation to body 502. For instance, extension 503 may be between two and ten times the length of body 502. Additionally, similarly to extension 503, extension 501 may have one or more fixation elements 512. In some cases, fixation elements 512 may be disposed at or near the distal end 526 of extension 501. In some cases, extension 501 may include one or more electrodes 510a-510e. As with electrodes 505a-505e, electrodes 510a-510e may be disposed proximate distal end 524 of extension 501, or may be spread out along the length of extension 501. In some embodiments, extension 501 may terminate at distal end 524 in an electrode. In some cases, one or more of the electrodes 510a-510e are spaced apart from a body 502 that is located in the coronary sinus 11 by a sufficient distance to electrically engage the left ventricle 27. In some instances, extension 501 may have one or more electrodes that are placed to align with the left atrium 23 to allow the pacing device 500 to sense and/or pace the left atrium 23 of the patient's heart. In some cases, extension 501 may be biased to form a shape such as a helical coil or one or more loops.

Figure 6:
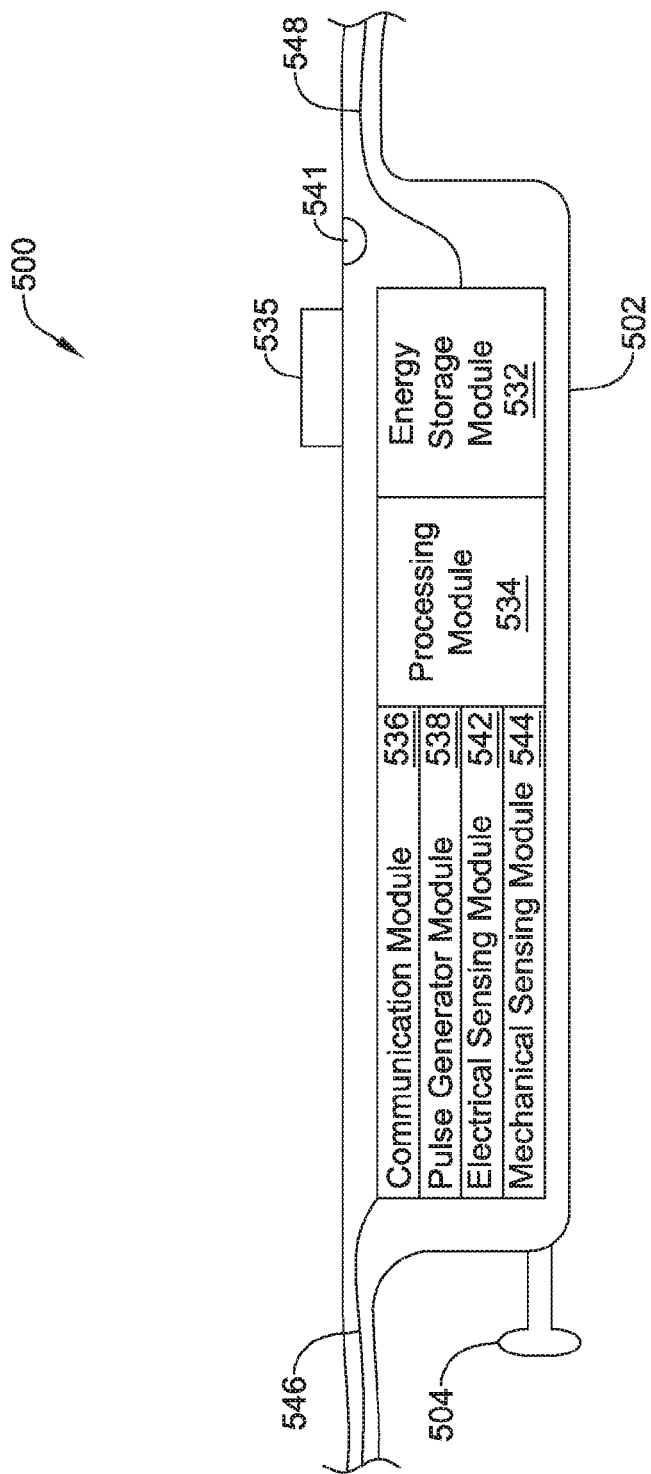
FIG. 6 is a schematic block diagram of the body of the illustrative pacing device of FIG. 5.

FIG. 6 is a schematic block diagram of one or more electronics modules that may be contained within body 502 of pacing device 500. In some instances, pacing device 500 may include energy storage module 532, processing module 534, communication module 536, pulse generator module 538, electrical sensing module 542, and/or mechanical sensing module 544. FIG. 6 also depicts conductors 546, 548 that may extend from one or more of modules 532, 534, 536, 538, 542, and/or 544 through extensions 503 and/or 501. Accordingly, in at least some embodiments, all of the electronic elements and energy storage modules of pacing device 500 may be contained within body 502, while only one or more conductors extend through extension 503 and/or extension 501 where included. Where pacing device 500 includes any of modules 532, 534, 536, 538, 542, and/or 544, the modules 532, 534, 536, 538, 542, and/or 544 may be similar to the modules of the same name described with respect to LCP 550 in FIG. 2.

Figure 7:
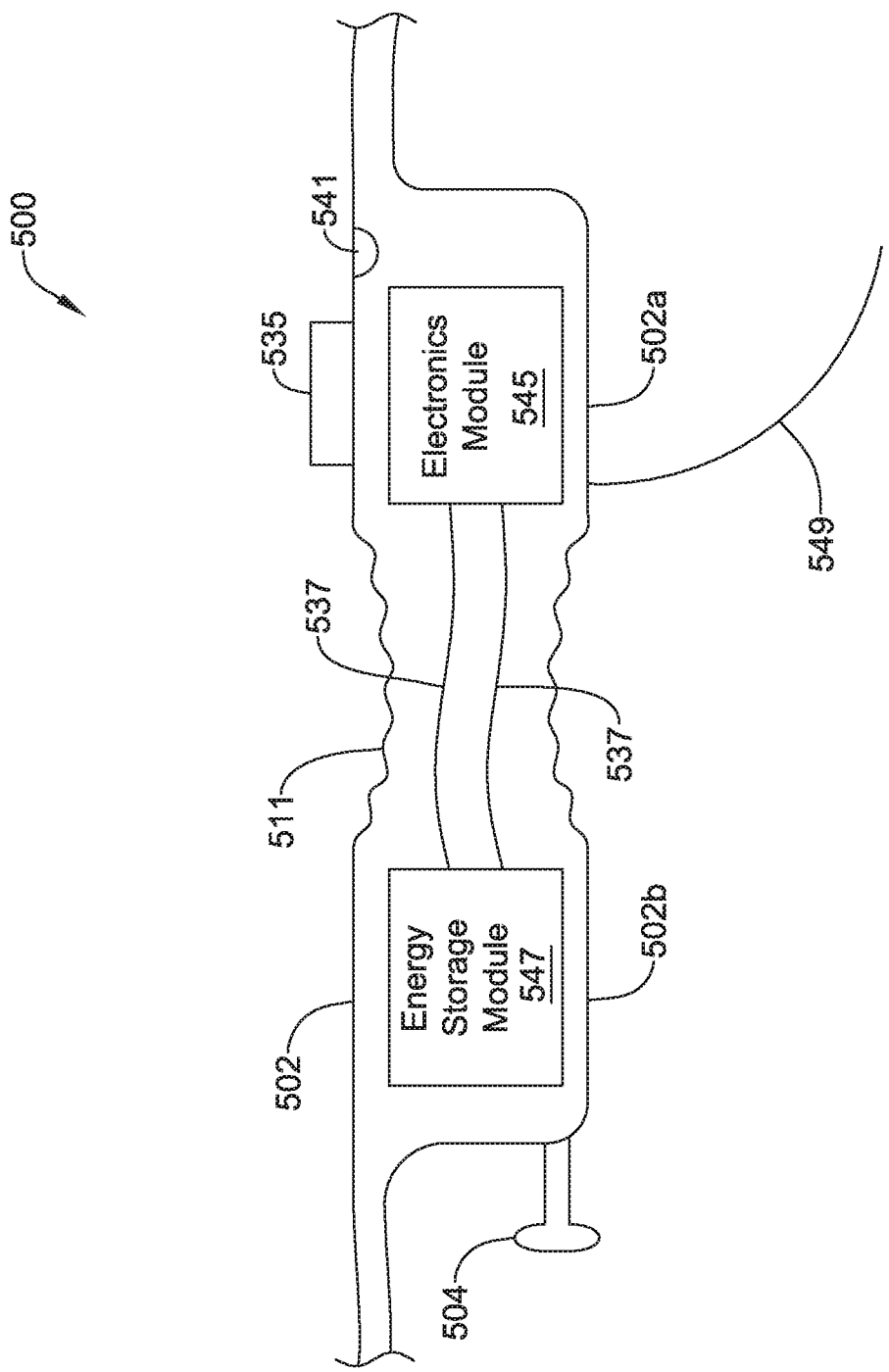
FIG. 7 is another schematic block diagram of a body of another illustrative pacing device.

FIG. 7 depicts an alternative embodiment of pacing device 500, and includes one or more features that may be additionally or alternatively combined, in other embodiments, with some or all of the features described with respect the pacing device 500 described in FIG. 6. Accordingly, in some instances, as depicted in FIG. 7, body 502 of pacing device 500 may be split into a rigid first portion 502a and a rigid second portion 502b. In some cases, rigid first portion 502a may partially, or wholly, house the electronics of pacing device 500, as depicted in FIG. 7 and may be represented by electronics module 545. Additionally, rigid second portion 502b may partially, or wholly, house the energy storage module of pacing device 500, as depicted in FIG. 7 and may be represented by energy storage module 547. However, in other cases, rigid first portion 502a may partially, or wholly, house the energy storage module, and rigid second portion 502b may partially, or wholly, house the electronics of pacing device 500. In some instances, rigid first portion 502a and rigid second portion 502b may be connected by a flexible connector 511. Flexible connector 511 may allow rigid first portion 502a and rigid second portion 502b to move and/or rotate with respect to each other, allowing each portion to be disposed at an angle relative to the other portion when implanted. Electronics module 545 and energy storage module 547 may be connected by one or more flexible electrical conductors 537 in the flexible connector 511. Although depicted in FIG. 7 as only including rigid first portion 502a and rigid second portion 502b, it is contemplated that body 502 of pacing device 500 may be split into any number of rigid portions connected by flexible connectors.

In some instances, pacing device 500 may include an eccentric bias element 549. Eccentric bias element 549 may be configured to bias the position of pacing device 500, when implanted, toward one side of coronary sinus 11. For instance, eccentric bias element 549 may be curved piece of biocompatible metal or polymer that extends away from body 502. When implanted, eccentric bias element 549 may press against a wall of coronary sinus 11 and impart an opposing force on body 502. This opposing force may act to push body 502 toward an opposite wall of coronary sinus 11, and bias the disposition of body 502 within coronary sinus 11. Biasing body 502 toward a side of coronary sinus 11 may help improve blood flow through coronary sinus 11 when pacing device 500 is implanted relative to blood flow through coronary sinus 11 when body 502 does not include eccentric bias element 549. In some embodiments, eccentric bias element 549 may include one or more fixation elements disposed proximate the end of eccentric bias element 549 that extends away from body 502. In such embodiments, eccentric bias element 549 may be configured to both bias the position of body 502 toward a side of coronary sinus 11 and secure the location of body 502 of pacing device 500 within coronary sinus 11. In such embodiments, body 502 may not include fixation element 535.

Figure 8:
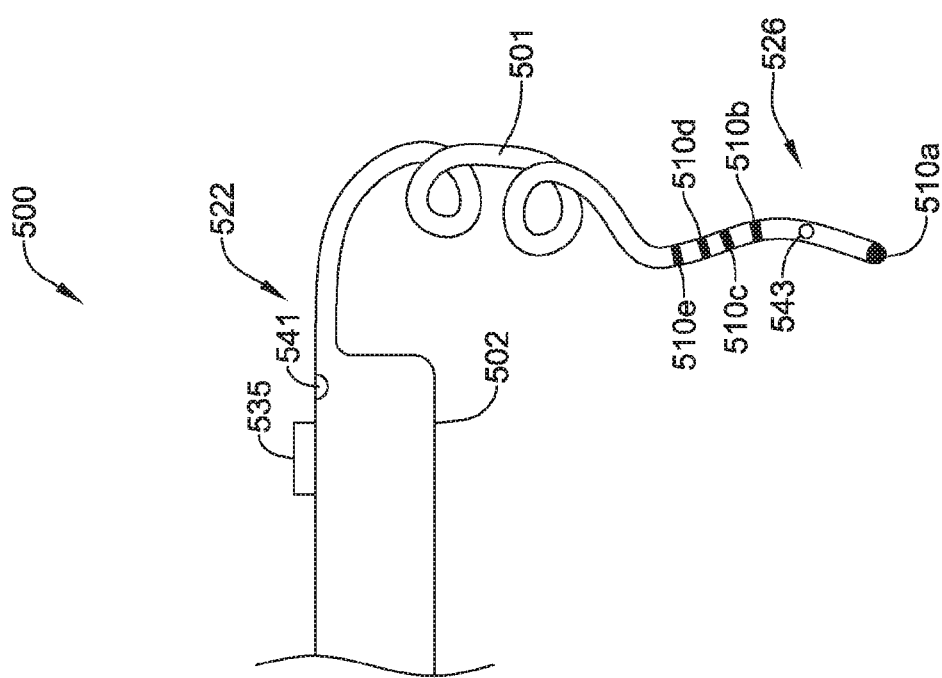
FIG. 8 is a schematic diagram of a distal portion of an illustrative pacing device.

FIG. 8 depicts an example where extension 501 may additionally or alternatively be biased to form a helical coil shape. When so provided, extension 501 may not include one or more fixation elements 512 disposed proximate distal end 526 of extension 501. Instead, extension 501 may be biased to form a helical coil shape that exerts an outward force on the great cardiac vein 13. When assuming the helical coil shape, the helical coil may have a diameter that is larger than the diameter of coronary sinus 11 and/or great cardiac vein 13. In such embodiments, when implanted, the friction between the helical coil shape of the extension 501 and the wall of coronary sinus 11 and/or great cardiac vein 13 may hold extension 501 in place within coronary sinus 11 and/or great cardiac vein 13. Even so, it is contemplated that in some cases extension 501 may include one or more fixation elements 512 in addition to being biased to form helical coil shape. Additionally, in embodiments where pacing device 500 does not include extension 501, pacing device 500 may include a fixation extension extending from distal end 522 of body 502. In such embodiments, the fixation extension may be biased to form a helical coil shape similar to extension 501 of FIG. 8. In some cases, the fixation extension may be shorter than extension 501 and may not include electrodes.

Figure 9A:
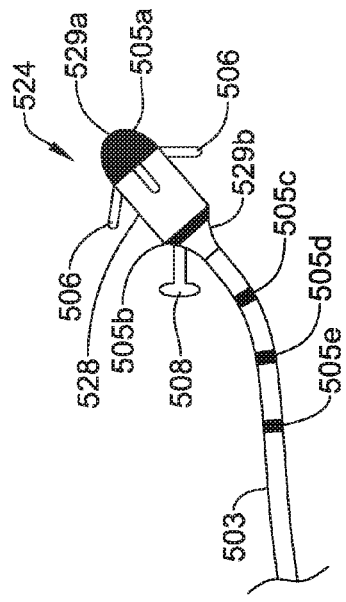
FIGS. 9A-9D are schematic diagrams of illustrative distal ends of an extension of a pacing device.
Figure 9B:
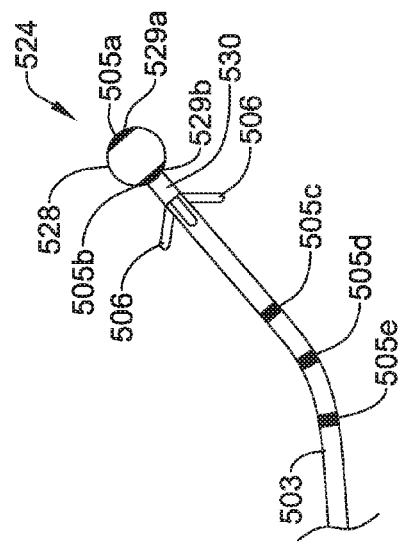
Figure 9C:
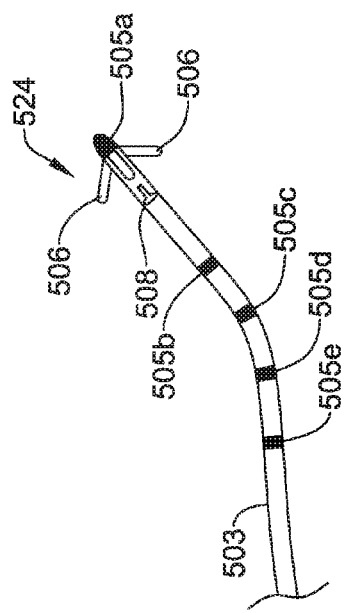

FIGS. 9A-9C depict illustrative embodiments of distal end 524 of extension 503. In the embodiment of FIG. 9A, extension 503 may be a long and flexible member, particularly in relation to body 502. For instance, extension 503 may be between two and ten times the length of body 502. In the embodiment of FIG. 9A, distal end 524 of extension 503 may maintain the same form as the rest of extension 503. In such embodiments, fixation elements 506 and docking hub 504 may extend directly from extension 503.

In the illustrative embodiment of FIG. 9B, extension 503 may again be a long and flexible member, particularly in relation to body 502. For instance, extension 503 may be between two and ten times the length of body 502. However, in the embodiment of FIG. 9B, extension 503 may terminate in a head 528. Head 528 may generally have a diameter greater than the diameter of the rest of extension 503 and may have a proximal end 529b and a distal end 529a. In the embodiment of FIG. 9B, extension 503 may connect directly to proximal end 529b of head 528. Docking hub 508 may also connect directly to proximal end 529b of head 528. As depicted in FIG. 9B, in at least some embodiments, fixation elements 506 may be disposed on head 528, and at least one of electrodes 505a-505e may also be disposed on head 528. In some cases, extension 503 may only include two electrodes, one to act as a cathode and one to act as an anode when pacing device 500 delivers electrical stimulation therapy to right atrium 21, and both electrodes may be disposed on head 528. In some cases, one of the electrodes may be on the distal tip 529a of the head 528.

FIG. 9C depicts another embodiment of extension 503. In the embodiment of FIG. 9C, extension 503 may be a long and flexible member, particularly in relation to body 502. For instance, extension 503 may be between two and ten times the length of body 502. As with the embodiment of FIG. 9B, in the embodiment of FIG. 9C, extension 503 may terminate in head 528. Head 528 may generally have a diameter greater than the diameter of the rest of extension 503 and may have a proximal end 529b and a distal end 529a. In the illustrative embodiment of FIG. 9C, extension 503 may connect to a side of head 528, while docking hub 508 may connect directly to proximal end 529b of head 528. As depicted in FIG. 9C, in at least some embodiments, fixation elements 506 may be disposed on head 528, and at least one of electrodes 505a-505e may also be disposed on head 528. In some cases, extension 503 may only include two electrodes, one to act as a cathode and one to act as an anode when pacing device 500 delivers electrical stimulation therapy to right atrium 21, and both electrodes may be disposed on head 528. In some cases, one of the electrodes may be on the distal tip 529a of the head 528.

Figure 9D:
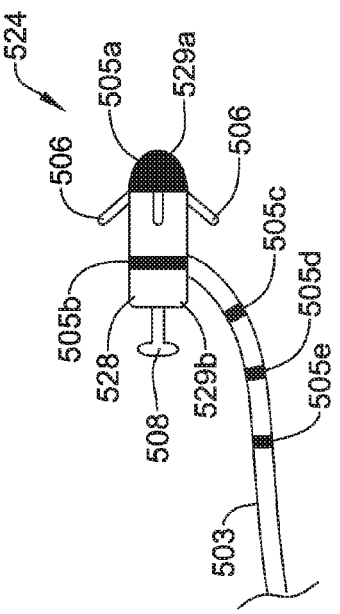

FIG. 9D depicts another embodiment of extension 503. In the embodiment of FIG. 9D, extension 503 may be a long and flexible member, particularly in relation to body 502. For instance, extension 503 may be between two and ten times the length of body 502. Extension 503 may terminate in head 528. In the embodiment of FIG. 9D, head 528 may generally be round or spherical in shape. Additionally, head 528 may have a diameter greater than the diameter of the rest of extension 503 and may have a proximal end 529b and a distal end 529a. Extension 503 may additionally have collar 530 connected to distal end 529a of head 528 and disposed between fixation elements 506 and head 528. As depicted in FIG. 9D, extension 503 may not have hub 508. In these cases, head 528 may directly be a part a coupling system for maneuvering distal end 524 to a desired location. Although shown with five electrodes 505a-e, in some cases, extension 503 may only include two electrodes, one to act as a cathode and one to act as an anode when pacing device 500 delivers electrical stimulation therapy to right atrium 21, and both electrodes may be disposed on head 528. In some cases, one of the electrodes may be on the distal tip 529a of the head 528.

FIGS. 10A and 10B are plan views of distal ends 524 of extension 503 where extension 503 includes alternative fixation elements. In the embodiment of FIG. 10A, instead of fixation elements 506 including one or more tines, fixation element 506 includes a helical wire coil or screw type member. In such embodiments, the helical wire coil may be screwed into septum 15 to secure the distal end 524 of extension 503 within right atrium 21.

In the embodiment of FIG. 10B, fixation elements 506 are depicted as talons. In such embodiments, the talons may be biased to have a predetermined shape. For example, when the talons are free to assume their predetermined shape, the talons may extend from distal end 524 of extension 503 and curl backwards away from the distal end 524 of extension 503. When implanted, the talons may be forced into a straight configuration by a delivery catheter or the like, and may be pushed into and puncture septum 15 before curling back into the right atrium, thereby securing the distal end 524 of extension 503 within right atrium 21.

Although the alternative fixation elements of FIGS. 10A and 10B were described with respect to extension 503, in some instances, the one or more fixation elements 512 and/or fixation mechanism 535 may also take any of the forms described with respect to FIGS. 10A and 10B. Further, in various embodiments, the specific fixation elements of extension 501, extension 503, and fixation mechanism 535 on body 502 may differ from each other, as desired.

Figure 11:
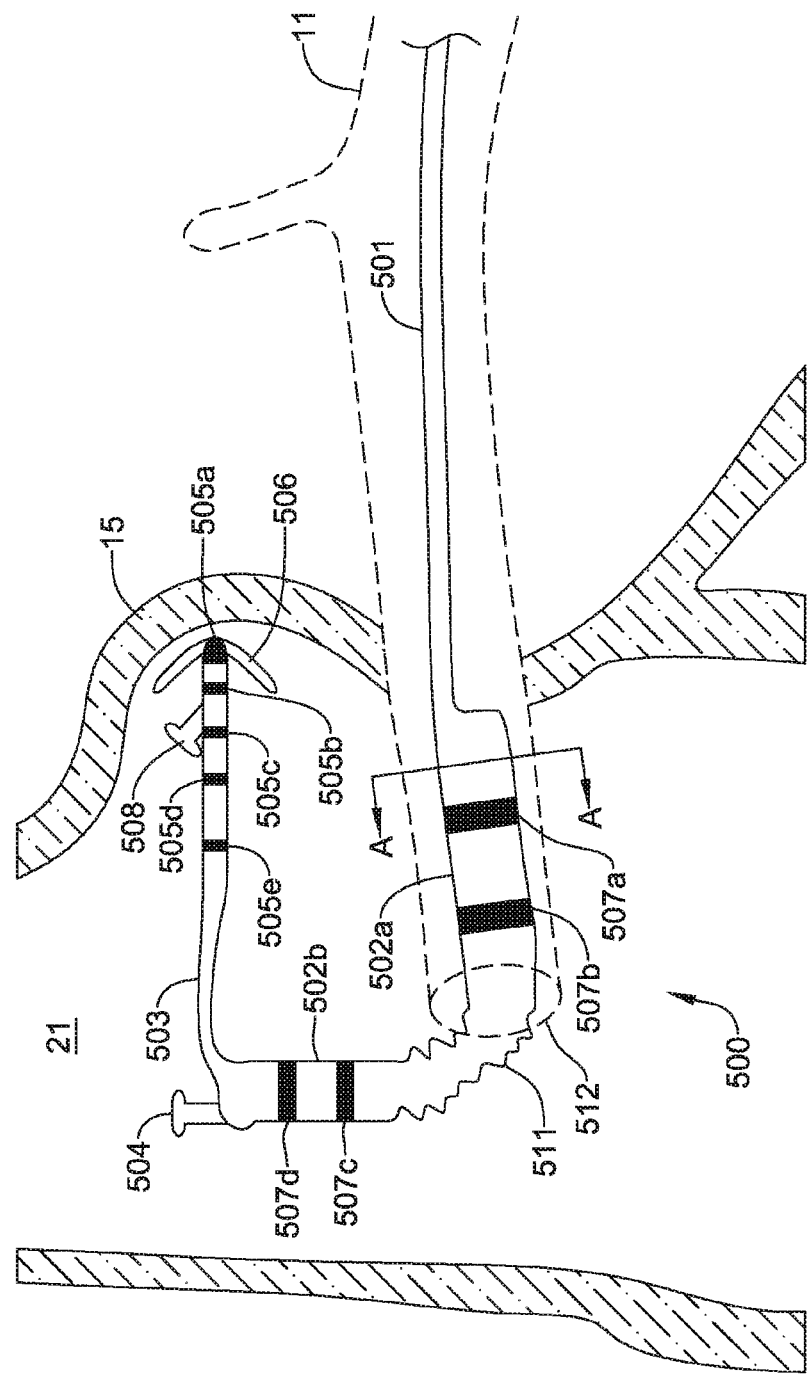
FIG. 11 is an illustrative diagram of a pacing device implanted within a patient's heart.

FIG. 11 depicts a close-up of plan view pacing of device 500 implanted within heart 10 of FIG. 1. In FIG. 11, pacing device 500 includes rigid first portion 502a and rigid second portion 502b. Pacing device 500 may be configured such that rigid first portion 502a is at least partially disposed within coronary sinus 11 as shown. In some instances, rigid first portion 502a may be completely disposed within coronary sinus 11. For instance, rigid first portion 502a may have a size sufficient to fit within coronary sinus 11 while still allowing blood flow through coronary sinus 11. As described with respect to FIG. 7, rigid first portion 502a may house some or all of the electronics of pacing device 500. Accordingly, when rigid first portion 502a is disposed completely within coronary sinus 11, all of the electronics of pacing device 500 may be disposed within coronary sinus 11. Additionally, as depicted in FIG. 11, pacing device 500 may be configured such that rigid second portion 502b is at least partially disposed within right atrium 21 of heart 10. For instance, rigid second portion 502b may have dimensions smaller than that of right atrium 21 to allow rigid second portion 502b to fit within right atrium 21. In some embodiments, rigid second portion 502b may be completely disposed within right atrium 21 of heart 10. As described with respect to FIG. 7, rigid second portion 502b may house some or all of the energy storage module of pacing device 500. Accordingly, when rigid second portion 502b is disposed completely within right atrium 21 of heart 10, the entire energy storage module of pacing device 500 may be disposed within right atrium 21. In other embodiments, the energy storage module may be placed in the rigid first portion 502a, and the rigid second portion 502b may house the electronics and be very light with less mass relative to rigid first portion 502a. These are just some examples of how the electronics and energy storage module may be split between rigid first portion 502a and rigid second portion 502b. In some cases, flexible connector 511 may extend through coronary sinus ostium 12 to connect rigid first portion 502a to rigid second portion 502b.

In the embodiment of FIG. 11, where only a portion of body 502 of pacing device 500 is disposed within coronary sinus 11, coronary sinus 11 may experience increased blood flow relative to embodiments where a greater portion, or all of, body 502 of pacing device 500 is disposed within coronary sinus 11. This is because the body 502 will present less of an occlusion to the coronary sinus 11. Additionally, where docking hub 504 is disposed on rigid second portion 502b and disposed within right atrium 21, docking hub 504 may be easier to access than if disposed in other locations, thereby allowing for easier retrieval of pacing device 500, should pacing device 500 need to be removed. Further, as at least a portion of body 502 of pacing device 500 resides within coronary sinus 11, pacing device 500 may place less stress on septum 15 of heart 10 where extension 503 attaches to septum 15. For instance, at least a portion of the mass of pacing device 500 may be supported by coronary sinus 11 as opposed to the entire mass of pacing device 500 hanging off of septum 15 by virtue of connection between extension 503 and septum 15, for example in embodiments where no weight of pacing device 500 is supported by coronary sinus 11. The septum 15 is often thin and potentially susceptible to damage if too large of a mechanical load is applied.

Figure 12:
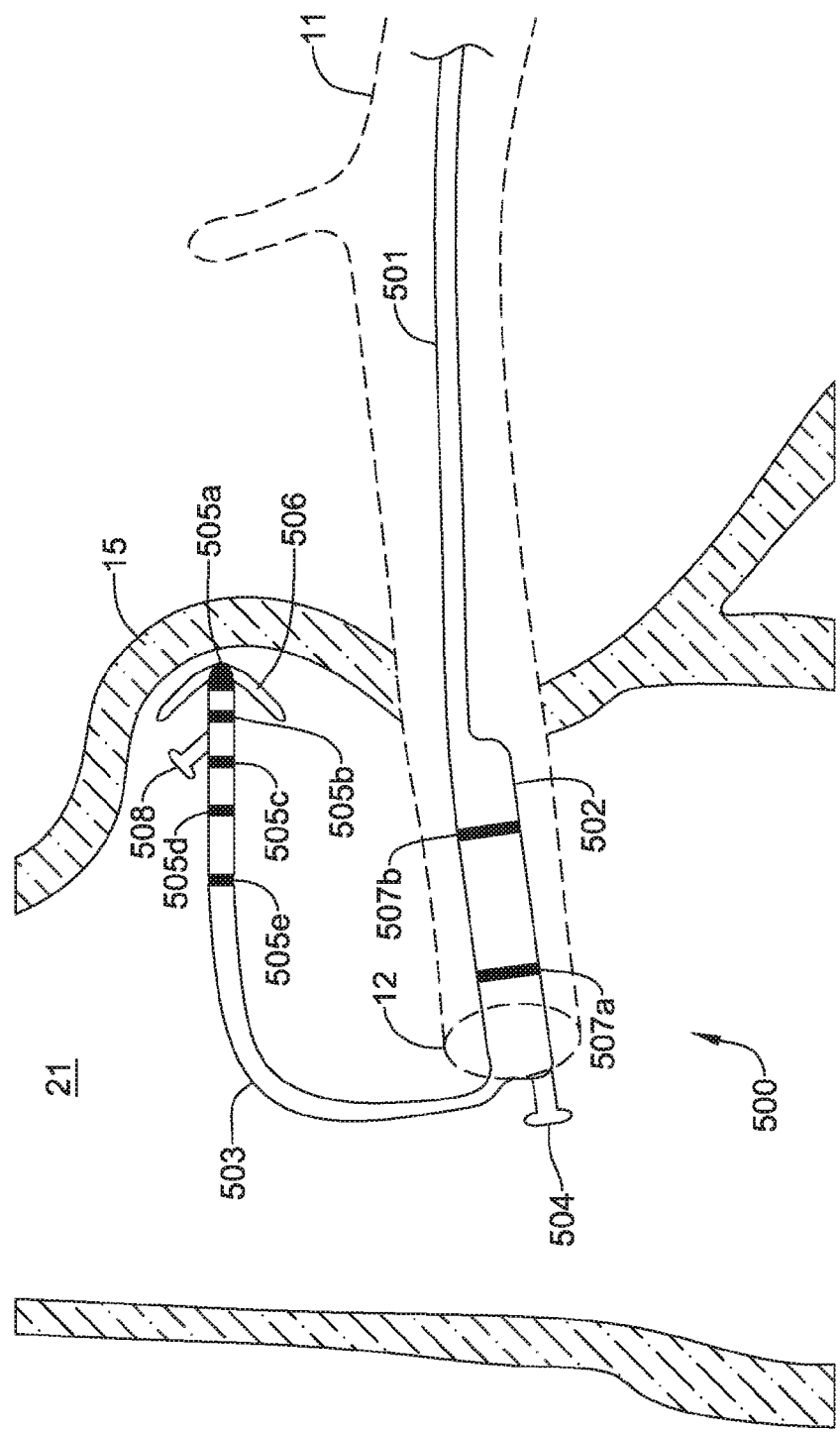
FIG. 12 is an illustrative diagram of another pacing device implanted within a patient's heart.

FIG. 12 depicts another close-up of pacing device 500 implanted within heart 10 of FIG. 1. In FIG. 12, body 502 of pacing device 500 may be a unitary housing, and pacing device may be configured such that the majority of body 502 is disposed within coronary sinus 11. In some cases, body 502 may have docking hub 504 extending from body 502, and pacing device 500 may be configured such that when pacing device 500 is implanted, docking hub 504 extends through coronary sinus ostium 12 and into the right atrium 21. Additionally, and in the embodiment shown, the extension 503 may be configured to extend through coronary sinus ostium 12 and over to the septum 15 of the right atrium 21.

In the embodiment of FIG. 12, where docking hub 504 extends through coronary sinus ostium 12, docking hub 504 may be easier to access than if disposed in other locations, thereby allowing for easier retrieval of pacing device 500, should pacing device 500 need to be removed. In the embodiment of FIG. 12, a majority of body 502 of pacing device 500 resides within coronary sinus 11. This may place less stress on septum 15 of heart 10 where extension 503 attaches to septum 15 because a majority of the mass of pacing device 500 may be supported by coronary sinus 11 as opposed to being supported by septum 15.

Figure 13B:
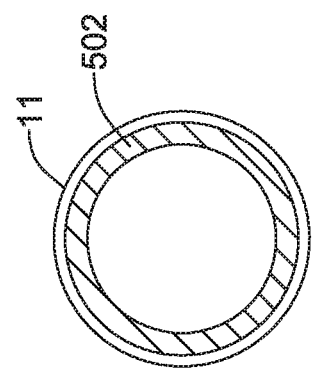
FIGS. 13A-13C are exemplary cross-sections of a pacing device.
Figure 13C:
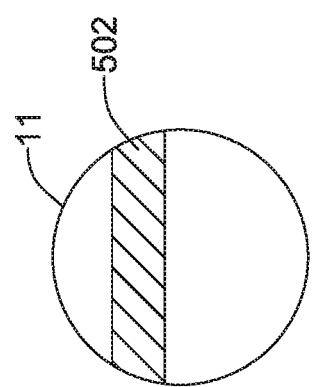
Figure 13A:
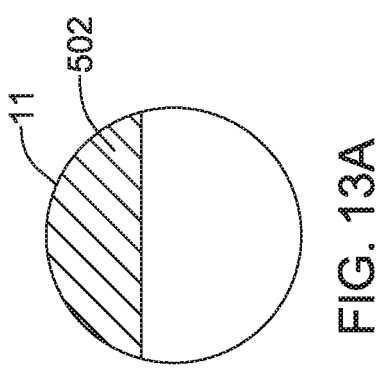

FIGS. 13A-13C are example cross-sections of body 502 of pacing device 500 as viewed along line A-A in FIG. 11. In these embodiments, body 502 of pacing device 500 may have a non-circular cross-section shape. For instance, as depicted in FIG. 13A, body 502 may have a circular segmented shape, with one rounded side and one flat side. In these embodiments, the circular segmented shape may generally conform to the shape of coronary sinus 11. Such a shape may allow for a greater and/or smoother flow of blood past body 502 within coronary sinus 11. FIG. 13B depicts another embodiment of body 502 that has a toroidal cross-sectional shape. FIG. 13C depicts another embodiment of body 502 that has a generally flat rectangular cross-section. In still other instances, body 502 may have a circular cross-section. Each of these cross-sectional shapes may have advantages for decreasing the amount of cross-sectional area of coronary sinus 11 that body 502 takes up, and may decrease the amount of turbulence that body 502 imparts to blood flowing past body 502. It is contemplated that the body 502 need not have the same cross sectional shape along its entire length. Also, in those instances where body 502 comprises a rigid first portion 502a and a rigid second portion 502b, each of rigid first portion 502a and rigid second portion 502b may have the same or different cross-section shapes.

Additionally, body 502 may have a cross-section diameter or area sufficient to fit within coronary sinus 11. Sizes of coronary sinus 11 may vary in humans between about 0.12 inches (3 mm) to about 0.6 inches (15 mm). Diameter of body 502 may range, in different embodiments, between about 0.1 inches (2.54 mm) to about 0.4 inches (10 mm). These sizes may allow body 502 to be implanted within different sized coronary sinuses while still allowing for sufficient blood flow through coronary sinus 11.

In some embodiments, pacing device 500 may be delivered to the implant site with a guide catheter, such as guide catheter 1000 of FIG. 14A. Guide catheter 1000 may generally be sized to be able to receive pacing device 500, a guide wire 1002, and positioning device 1004 within a lumen of the guide catheter 1000. When disposed within guide catheter 1000, pacing device 500 may be connected to positioning device 1004 by interlocking mechanism 1006. Interlocking mechanism 1006 may releasably couple with docking hub 504 of body 502.

To deliver pacing device 500 to the implant site, pacing device 500 may be threaded over guide wire 1002, which may have already been positioned within coronary sinus 11 or down the great cardiac vein 13. In some cases, guide wire 1002 may be threaded through guide wire port 433 and out guide wire port 431, as depicted in FIG. 14A. Guide catheter 1000, including pacing device 500, may then be advanced over the guide wire 1002. Once in position, such as in the coronary sinus 11 of the heart, the guide catheter 1000 may be retracted, for example in the direction of arrows 1010, thereby exposing pacing device 500, as depicted in FIG. 14B. The pacing device 500 may be kept in position by positioning device 1004. In other embodiments, instead of retracting guide catheter 1000, positioning device 1004 may be used to push pacing device 500 out the end of guide catheter 1000.

In some embodiments, positioning device 1004 may be semi-flexible, but retain sufficient rigidity to impart force to pacing device 500 when maneuvered. For instance, once guide catheter 1000 is in position, and guide catheter 1000 is then retracted, a user may manipulate positioning device 1004 to impart force on pacing device 500 through docking hub 504. In this manner, the user may maneuver pacing device 500 to a desired location. Once in position, the user may decouple interlocking mechanism 1006 from docking hub 504, and may retract guide wire 1002 and guide catheter 1000, including positioning device 1004. In other embodiments, after decoupling positioning device 1004 from docking hub 504, the user may maneuver positioning device 1004 and couple interlocking mechanism 1006 to docking hub 508 of the extension 503. The user may then maneuver distal end 524 of extension 503 to a desired location (e.g. to the septum of the right atrium) before decoupling positioning device 1004 from docking hub 508. Once decoupled, the user may then retract guide catheter 1000 from the body, including positioning device 1004.

Figure 15:
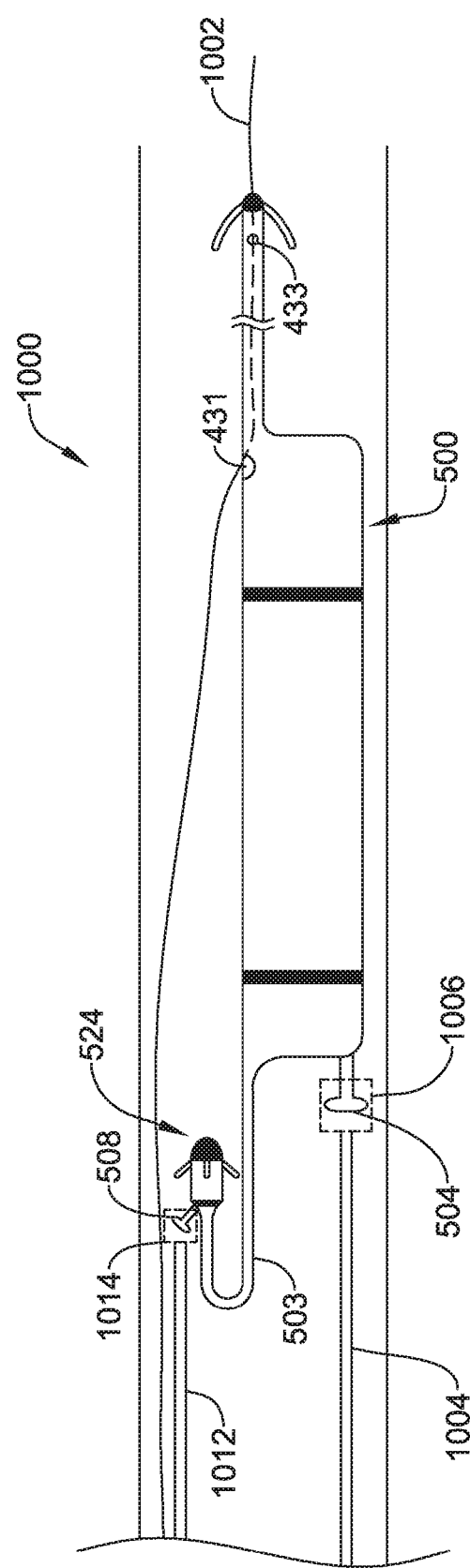
FIG. 15 is an illustrative diagram of an illustrative pacing device being delivered within a guide catheter.

In some instances, instead of decoupling interlocking mechanism 1006 and positioning device 1004 from docking hub 504 and coupling interlocking mechanism 1006 and positioning device 1004 to docking hub 508, guide catheter 1000 may include two separate positioning devices 1004, 1012, such as depicted in FIG. 15. Positioning device 1012 may additionally comprise interlocking mechanism 1014 for coupling to docking hub 508. This may allow a user to maneuver body 502 into place using positioning device 1004 and to maneuver distal end 524 of extension 503 into place using positioning device 1012. In still other instances, a single positioning device, such as positioning device 1004, may include multiple interlocking mechanisms. For example, a first interlocking mechanism may interlock with docking hub 504, which a second interlocking mechanism may interlock with docking hub 508. A user may then use positioning device 1004 to position both pacing device 1004 and distal end 524 of extension 503.

FIGS. 16A and 16B illustrate an illustrative positioning device 1004 and interlocking mechanism 1006. In the example shown in FIGS. 16A and 16B, positioning device 1004 may include a sheath 1051. In some instances, sheath 1051 may include one or more structural features that impart a sufficient level of rigidity to allow a user to push, pull, and otherwise move positioning device 1004 and body 502 or distal end 524 of extension 503 when positioning device is coupled to either body 502 or distal end 524 of extension 503. For instance, in some embodiments, sheath 1051 may be a braided sheath, or have a braided covering or inner support member coupled to sheath 1051. In other embodiments, positioning device 1004 may include a coiled wire coupled to sheath 1051.

In the example shown, interlocking mechanism 1006 may include members 1053 which terminate at one end in prongs 1055. In some cases, members 1053 may extend all the way down sheath 1051 and may be manipulated by a user to transition prongs 1055 between an open position (see FIG. 16A) and a closed position (see FIG. 16B). FIG. 16A depicts prongs 1055 in an open configuration and disposed proximate docking hub 504. When coupling interlocking device 1006, a user may position prongs 1055 in a position close-to or around docking hub 504. Once in position, the user may manipulate members 1053 to transition prongs 1055 from the open position into the closed position. FIG. 16B depicts prongs 1055 in the closed position around docking hub 508.

In the example shown in FIGS. 16A and 16B, sheath 1051 may be able to be moved relative to members 1053. For example, in the open position, sheath 1051 may not be disposed around prongs 1055 as shown in FIG. 16A. Prongs 1055 may be biased such that when prongs 1055 are outside of the sheath 1051, prongs 1055 may expand to a greater extent than the diameter of sheath 1051. To transition prongs 1055 to the closed position, a user may simply slide sheath 1051 relative to members 1053, such as toward prongs 1055. As sheath 1051 is slid toward prongs 1055, at least a portion of prongs 1055 may be compressed by sheath 1051. This compression of prongs 1055 may cause prongs 1055 to transition to the closed position, as depicted in FIG. 16B.

FIGS. 17A-17C depict another embodiment of positioning device 1004 and interlocking mechanism 1006. FIG. 17A depicts positioning device 1004 and interlocking mechanism 1006 disposed proximate a docking hub 504. In these embodiments, positioning device 1004 may include a sheath 1051, as described with respect to FIGS. 16A-16B. Interlocking mechanism 1006 may include inflation member 1061 and balloon 1063. In some cases, balloon 1063 may have a generally toroidal shape, or any other suitable shape with a hole or recess. To couple to docking hub 504, a user may position balloon 1063 in an un-inflated state around docking hub 504, as shown in FIG. 17B. Once balloon 1063 is positioned around docking hub 504, a user may inflate balloon 1063 by injecting inflation media through inflation member 1061 and into balloon 1063. When balloon 1063 inflates, it expands around docking hub 504, thereby securing docking hub 504 to balloon 1063 and thus to positioning device 1004, as depicted in FIG. 17C. When coupled, a user may maneuver positioning device 1004, and consequently body 502 attached to docking hub 504, into a desired position.

FIGS. 18A-18D depict additional embodiments of positioning device 1004 and interlocking mechanism 1006. FIG. 18A depicts positioning device 1004 and extension 503 disposed within guide catheter 1000. In the example of FIG. 18A, head 528 may be generally round or spherical, but in other cases head 528 may take other shapes. In these examples, head 528, and extension 503 more generally, may not include a hub. Instead, coupling of positioning device 1004 to extension 503 may be accomplished by a coupling directly with head 528. As depicted in FIG. 18A, positioning device 1004 may be a generally hollow tube with interlocking mechanism 1006 disposed at one end. Interlocking mechanism 1006 may generally comprise arms 1011 and cut-out 1015. Cut-out 1015, as depicted in FIG. 18A, may comprise a slot extending away from the end of positioning device 1004 and a round cut-out disposed proximate the end of positioning device 1004. Arms 1011 extend beyond the round cut-out toward the end of interlocking mechanism 1006. The round cut-out and the arms may be sized to engage with head 528, as seen in FIG. 18A. For instance, the round cut-out may be slightly smaller than head 528 such that arms 1011 bend around head 528 and firmly secure 528 to positioning device 1004. Arms 1011 may be made from a material or designed in such a way that arms 1011 are able to flex due to external forces, for example when head 528 is inserted in the round cut-out, but rigid enough to return to an unstressed state when the external force is removed.

Once guide catheter has been maneuvered into a desired position, the end of positioning device 1004 including interlocking mechanism 1006 which is coupled to head 528, may be pushed out of guide catheter 1000, or guide catheter 1000 may be retraced relative to positioning device 1004 and extension 503. FIG. 18B shows the portion of positioning device 1004 including interlocking mechanism 1006, and coupled to extension 503, outside of guide catheter 1000. When head 528 is coupled to interlocking mechanism 1006, extension 503 may be free to rotate about head 528 as head 528 is able to rotate within the round cut-out. However, while interlocking mechanism 1006 and extension 503 are disposed within guide catheter 1000, the walls of guide catheter 1000 may constrain such rotation. Once outside of guide catheter 1000, extension 503 may rotate about interlocking mechanism 1006, as seen in FIG. 18C, which shows a side view of positioning device 1004 coupled to head 528. Where cut-out 1015 includes a slot, the slot may allow for a greater range of rotation of head 528 and extension 503 by allowing collar 530 and/or other portions of extension 503 to rotate into the slot. The rotation of head 528 when coupled to interlocking mechanism 1006 may be important for properly orienting head 528 with respect to the desired implant site. For instance, a user may manipulate positioning device 1004 to position positioning device 1004, and more specifically the end of positioning device 1004 including interlocking mechanism 1006, at a desired implant location. Once positioning device 1004 is in place, implanting head 528 may involve decoupling head 528 from interlocking mechanism 1006. However, once head 528 is decoupled, the user may no longer have any control over the positioning of head 528. Accordingly, allowing for head 528 to rotate when coupled to interlocking mechanism 1006 may assist in properly orienting extension 503 for implantation. In some embodiments, extension 503 may have a coiled or otherwise bent shape. Once extension 503 is free from the constraints of guide catheter 1000, extension 503 may twist into its coiled or otherwise bent shape. As extension 503 attempts to take on its coiled or otherwise bent shape, extension 503 may rotate about interlocking mechanism 1006 and orient extension 503 in a desired orientation, as seen in FIG. 18C.

Once positioning device 1004 is positioned at the implant location, a stylet or other pushing member 1018 may be inserted into the lumen of positioning device 1004. Stylet 1018 may be advanced toward interlocking mechanism 1006 and head 528. As stylet 1018 contacts head 528, stylet 1018 applies pushing forces head 528 to decouple head 528 from interlocking mechanism 1006, for example by pushing head 528 out of arms 1011 and cut-out 1015. Positioning device 1004 may then be retracted as head 528 is held in place by fixation member 506. It should be understood that although the embodiments of FIGS. 18A-18D are described with respect to positioning device 1004 and extension 503, a similar interlocking mechanism may be used in conjunction with body 502.

Figure 19:
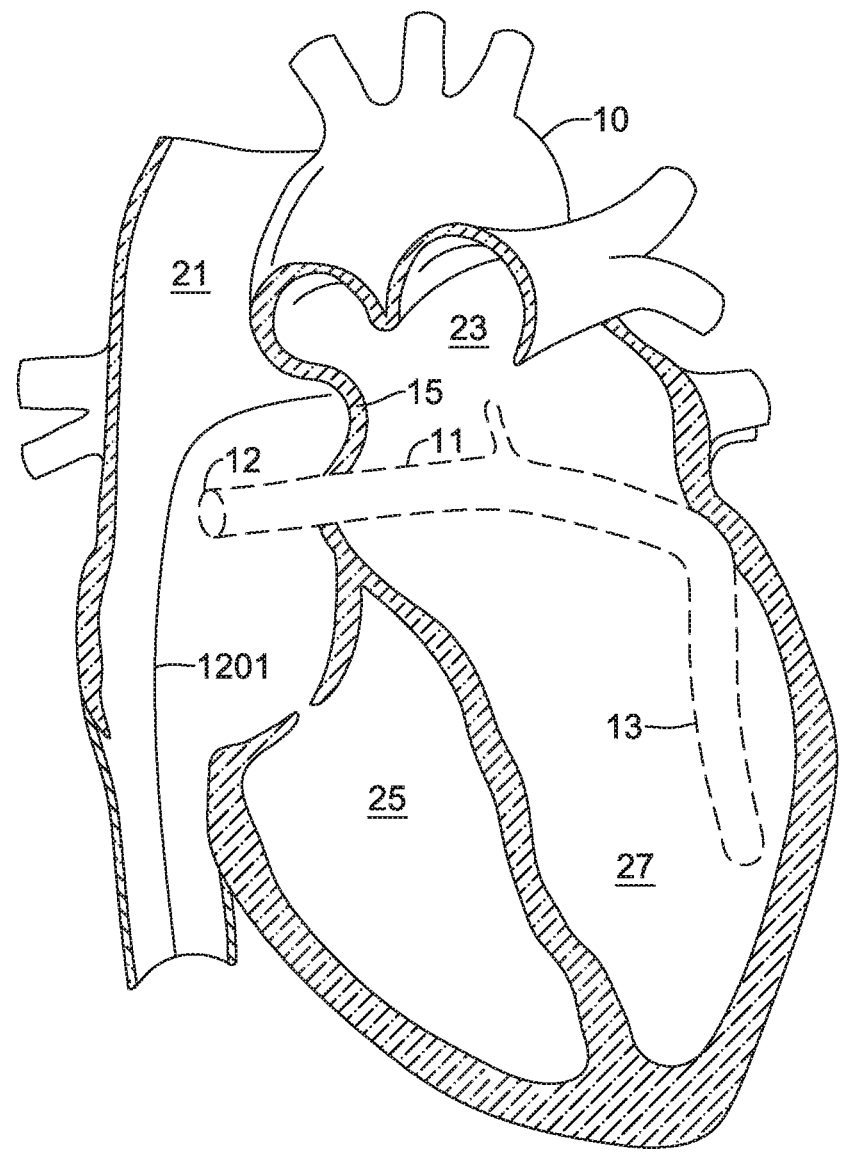
FIGS. 19-24 are a series of diagrams that show delivery of an illustrative pacing device into a patient's heart.

FIGS. 19-24 depict the use of a guide wire and guide catheter 1000 in the implantation of pacing device 500 within heart 10. In some embodiments, implanting pacing device 500 within heart 10 may begin by positioning a guide wire within heart 10, such as guide wire 1201. In some instances, guide wire 1021 may have one or more radiopaque markers disposed on an end of guide wire 1201. Such radiopaque markers may allow for easier viewing of guidewire 1201 through one or more medical imaging systems as the guide wire 1201 is maneuvered into position with the heart 10. In some embodiments, the radiopaque markers may be spaced apart from each other by a known distance. In such embodiments, by counting the number of radiopaque markers between two features within heart 10, a distance may be determined between the two features. In some embodiments, pacing device 500 may be manufactured in a variety of sizes, or various portions of pacing device 500, such as body 502 and extension 503, may be manufactured in various sizes and lengths. By determining a distance between different features of the patient's heart 10, for instance between the coronary sinus ostium 12 and septum 15 in the right atrium 21, as depicted in FIG. 19, an appropriate sized body 502 or extension 503 may be selected for the particular patient.

Figure 20:
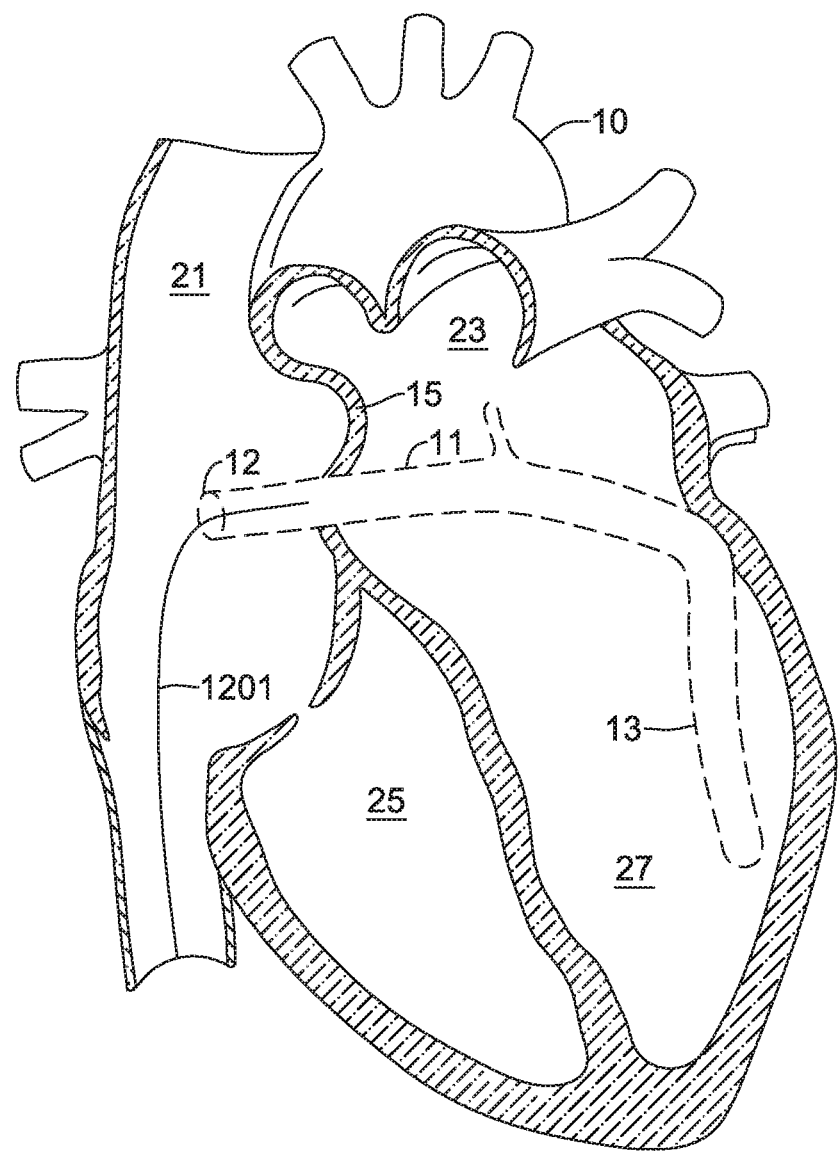
Figure 21:
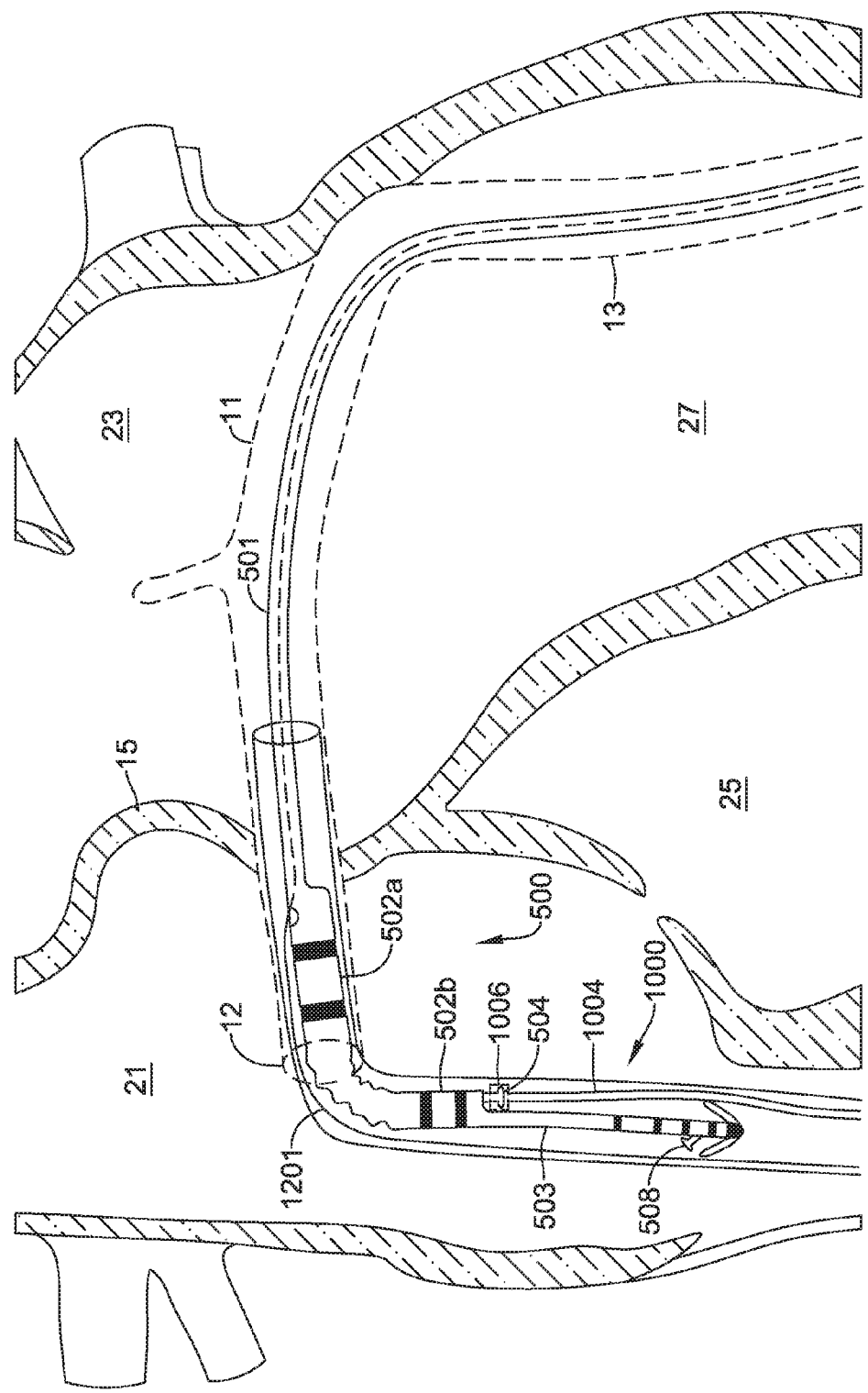

After measuring distances between various features of heart 10, or in embodiments where such measurements are not needed, guide wire 1201 may then be positioned within the coronary sinus 11, as depicted in FIG. 20. In some embodiments, guide wire 1201 may be maneuvered all the way through coronary sinus 11 and into great cardiac vein 13. Once guide wire 1201 is in place, guide catheter 1000, containing pacing device 500, may be maneuvered over guide wire 1201 into place within heart 10. FIG. 21 depicts guide catheter 1000 and pacing device 500 positioned within coronary sinus 11.

Figure 22:
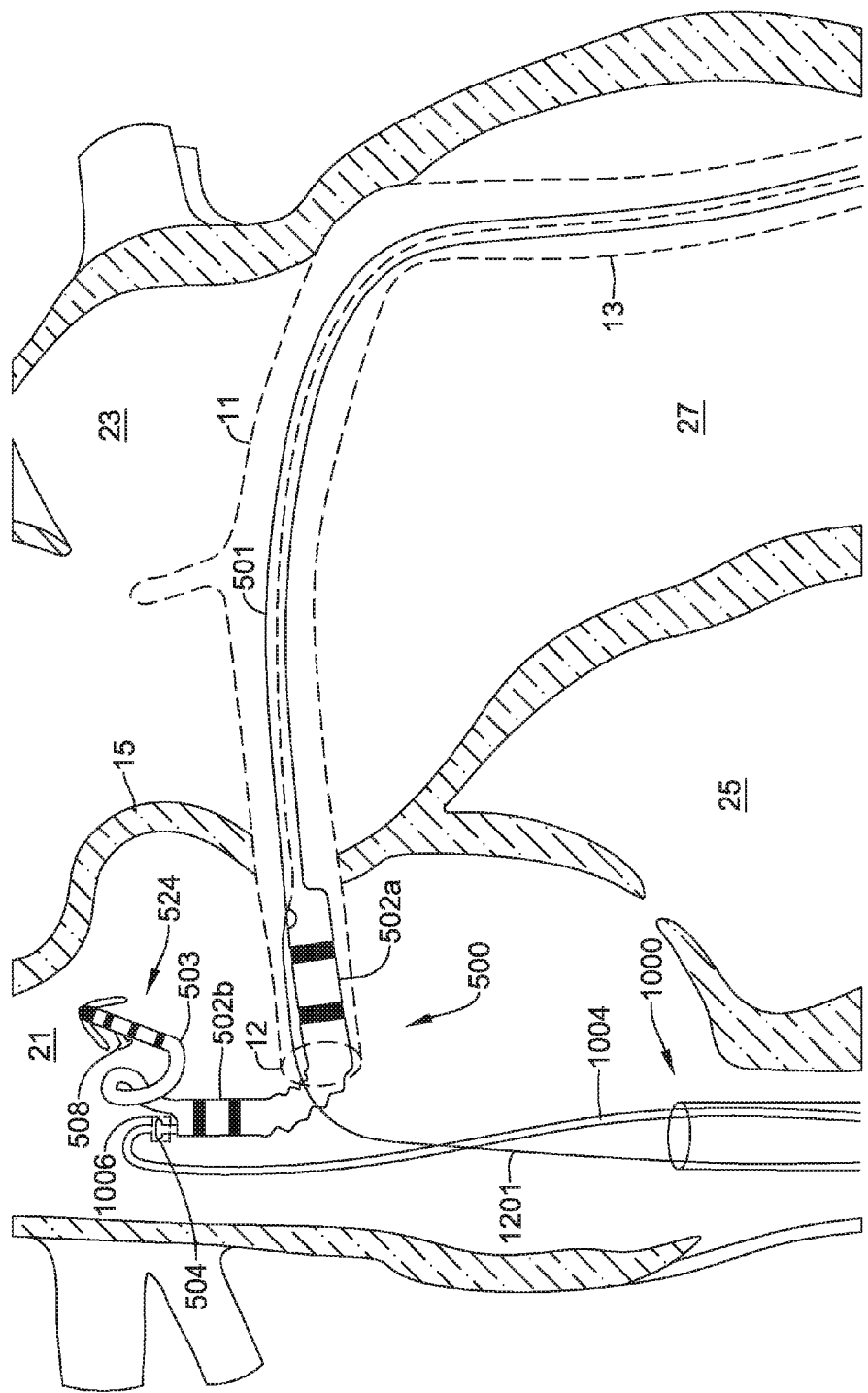
Figure 23:
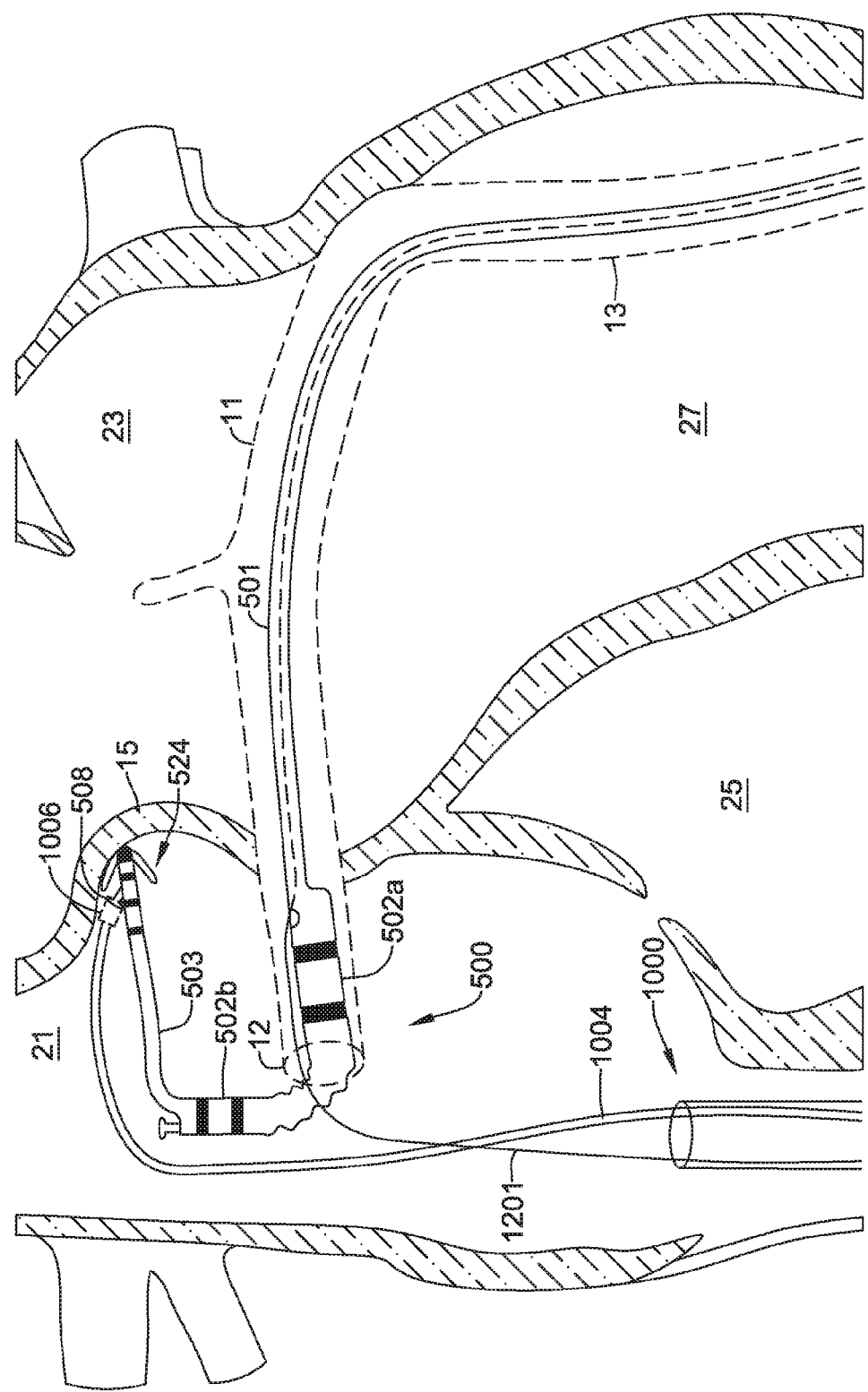
Figure 24:
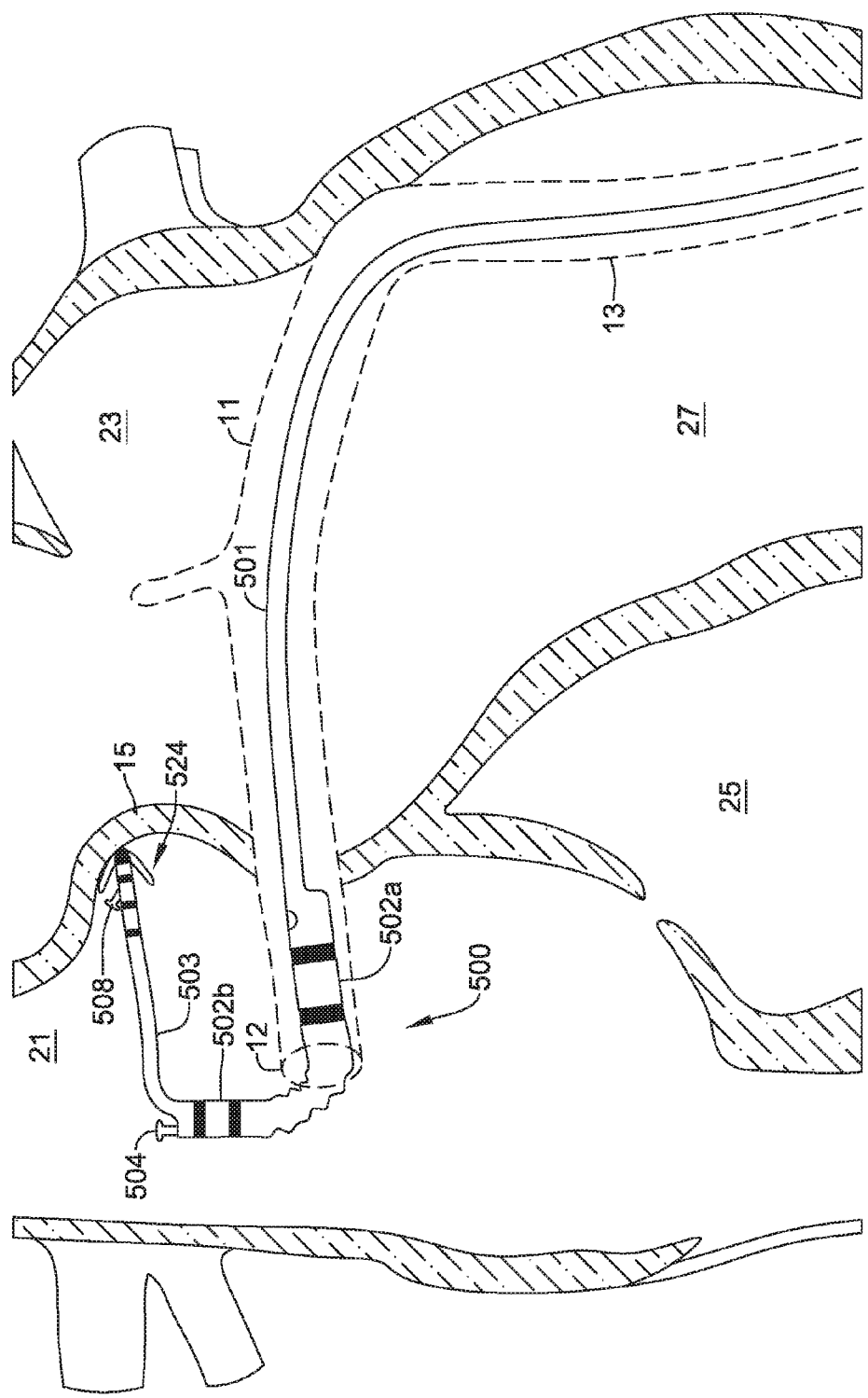

Once pacing device 500 is in position, the guide catheter 1000 may be retracted. FIG. 22 depicts an example of how pacing device 500 may look after guide catheter 1000 has been retracted. In some embodiments, body portions 502a and 502b may be biased into a particular configuration such that when the guide catheter 1000 is retracted, body portions 502a and 502b assume the configuration shown in FIG. 22. In other embodiments, body portions 502a and 502b may not be biased into a particular configuration, and positioning device 1004 may be maneuvered to position body portion 502b with respect to body portion 502a as shown in FIG. 22. Once body portions 502a and 502b are in position, interlocking mechanism 1006 may be decoupled from docking hub 504, and then coupled to docking hub 508. Positioning device 1004 may then be maneuvered to position extension 503 into position, for example, with distal end 524 disposed proximate septum 15, as depicted in FIG. 23. In other embodiments, guide catheter 1000 may include a second positioning device that includes a second interlocking mechanism that is coupled to docking hub 508 during implantation of pacing device 500. In these embodiments, instead of coupling interlocking mechanism 1006 to docking hub 508, the second positioning device may be maneuvered to position extension 503 into place. Once extension 503 has been positioned appropriately, guide catheter 1000, including positioning device 1004, and guide wire 1201 may be retracted all the way out of the patient, leaving pacing device 500 implanted within heart 10 as shown in FIG. 24.

Those skilled in the art will recognize that the present disclosure may be manifested in a variety of forms other than the specific embodiments described and contemplated herein. For instance, as described herein, various embodiments include one or more modules described as performing various functions. However, other embodiments may include additional modules that split the described functions up over more modules than that described herein. Additionally, other embodiments may consolidate the described functions into fewer modules.

Although various features may have been described with respect to less than all embodiments, this disclosure contemplates that those features may be included on any embodiment. Further, although the embodiments described herein may have omitted some combinations of the various described features, this disclosure contemplates embodiments that include any combination of each described feature. Accordingly, departure in form and detail may be made without departing from the scope and spirit of the present disclosure as described in the appended claims.

What is claimed is:

1. An implantable medical device (IMD), the IMD comprising:
   a housing having a proximal end and a distal end;
   a first set of one or more electrodes connected to but spaced apart from the housing; and
   a controller disposed within the housing, wherein the controller is configured to:
   sense cardiac electrical signals, and
   deliver electrical stimulation pulses via the first set of one or more electrodes; and
   wherein a first portion of the housing is configured to be disposed at least partly within a coronary sinus of a patient's heart and a second portion of the housing is configured to be disposed outside of the coronary sinus and at least partly within a right atrium of the patient's heart.

2. The IMD of claim 1, wherein the housing further comprises a fixation element disposed on the portion of the housing that is configured to be disposed within the coronary sinus.

3. The IMD of claim 1, wherein the housing further comprises an eccentric bias element disposed on the portion of the housing that is configured to be disposed within the coronary sinus.

4. The IMD of claim 1, wherein the housing further comprises a docking hub disposed proximate the proximal end of the housing.

5. The IMD of claim 1, wherein the housing comprises at least a first discrete section and a second discrete section, and wherein the first discrete section is configured to be disposed at least partially within the coronary sinus and the second discrete section is configured to be disposed within the right atrium of the patient's heart.

6. The IMD of claim 5, wherein the first discrete section and the second discrete section are connected by a flexible connector section.

7. The IMD of claim 1, wherein at least a portion of the housing has a non-circular cross-section.

8. The IMD of claim 1, wherein the first set of one or more electrodes are disposed on a first extension extending from the housing.

9. The IMD of claim 8, wherein the first extension has a proximal end and a distal end, and wherein the proximal end of the first extension is connected to the housing, and wherein a fixation element is positioned adjacent the distal end.

10. The IMD of claim 8, wherein a docking hub is positioned adjacent the distal end of the first extension.

11. An implantable medical device (IMD), the IMD device comprising:
    a housing having a proximal end and a distal end;
    a first set of one or more electrodes operatively connected to but spaced apart from the housing; and
    a controller disposed within the housing, wherein the controller is configured to:
    communicate with one or more medical devices spaced from the IMD;
    sense cardiac electrical signals; and
    deliver electrical stimulation pulses via the first set of one or more electrodes; and
    wherein the housing is configured to be disposed at least partly within a coronary sinus of a patient's heart, and wherein at least a portion of the housing has a non-circular cross-section.

12. The IMD of claim 11, wherein the housing further comprises a first portion and a second portion, and wherein the first a portion of the housing is configured to be disposed at least partly within the coronary sinus of the patient's heart and a second portion of the housing is configured to be disposed outside of the coronary sinus and at least partly within a right atrium of the patient's heart, wherein at least a portion of the first portion of the housing has a non-circular cross-section.

13. The IMD of claim 11, wherein the first set of electrodes is configured to be disposed within the right atrium of the patient's heart, and the controller is configured to deliver electrical stimulation to the right atrium of the patient's heart via the first set of electrodes.

14. The IMD of claim 11, wherein the IMD further comprises a second set of one or more electrodes, and wherein the second set of one or more electrodes are configured to be disposed within the coronary sinus.

15. An implantable medical device (IMD), the IMD device comprising:
    a housing having a rigid first portion and a rigid second portion, wherein the rigid first portion and the rigid second portion are physically connected by a flexible connector;
    a controller disposed within the housing, wherein the controller is configured to:
    communicate with one or more medical devices spaced from the IMD;
    sense cardiac electrical signals; and
    deliver electrical stimulation pulses via a first set of one or more electrodes;
    wherein the rigid first portion of the housing is configured to be disposed at least partly within the right atrium of the patient's heart, and the rigid second portion of the housing is configured to be disposed at least partly within a coronary sinus of the patient's heart; and
    a fixation element for holding the rigid second portion of the housing at least partly within the coronary sinus of the patient's heart.

16. The IMD of claim 15, wherein the housing comprises a docking hub disposed on the rigid first portion.

17. The IMD of claim 15, wherein the first set of one or more electrodes are provided on an atrial extension extending from the rigid first portion, wherein the atrial extension comprises a fixation element configured to fix the atrial extension to the an atrium wall of the atrium of the patient's heart.

18. The IMD of claim 17, wherein the fixation element comprises one or more of tines, helical coils, and metal talons.

19. The IMD of claim 15, further comprising a second set of one or more electrodes, wherein the second set of one or more electrodes are provided on a ventricle extension extending from the rigid second portion further into the coronary sinus of the patient's heart, wherein the ventricle extension comprises a fixation element configured to fix the ventricle extension to a wall of the coronary sinus of the patient's heart.

20. The IMD of claim 19, wherein the controller is further configured to deliver electrical stimulation pulses via the second set of one or more electrodes.

* * * * *